(12) United States Patent
Kaneko

(10) Patent No.: US 7,450,151 B2
(45) Date of Patent: Nov. 11, 2008

(54) ENDOSCOPE IMAGE PROCESSING APPARATUS

(75) Inventor: Kazuma Kaneko, Sagamihara (JP)

(73) Assignee: Olympus Corporation, Tokyo (JP)

( * ) Notice: Subject to any disclaimer, the term of this patent is extended or adjusted under 35 U.S.C. 154(b) by 610 days.

(21) Appl. No.: 10/503,012

(22) PCT Filed: Mar. 14, 2003

(86) PCT No.: PCT/JP03/03071

§ 371 (c)(1),
(2), (4) Date: Jul. 29, 2004

(87) PCT Pub. No.: WO03/075753

PCT Pub. Date: Sep. 18, 2003

(65) Prior Publication Data

US 2005/0157168 A1 Jul. 21, 2005

(30) Foreign Application Priority Data

Mar. 14, 2002 (JP) ............................. 2002-070498
Mar. 11, 2003 (JP) ............................. 2003-065561

(51) Int. Cl.
*A61B 1/04* (2006.01)
*H04N 7/18* (2006.01)

(52) U.S. Cl. .......................................... 348/72; 348/74

(58) Field of Classification Search .................. 348/72, 348/74, 65, 76, 68, 69, 70, 71, 42, 43, 44, 348/45, 48, 50, 57, 58, 60, 78, 66, 79, 67, 348/46, 47, 59, 661; 382/128, 133, 134; 600/109, 178, 160, 100, 110, 114, 180, 181, 600/152, 476, 168, 101, 118, 145
See application file for complete search history.

(56) References Cited

U.S. PATENT DOCUMENTS

| | | | | |
|---|---|---|---|---|
| 5,675,378 | A * | 10/1997 | Takasugi et al. | 348/65 |
| 6,491,628 | B1 * | 12/2002 | Kobayashi | 600/168 |
| 6,902,527 | B1 * | 6/2005 | Doguchi et al. | 600/109 |
| 6,992,694 | B2 * | 1/2006 | Abe | 348/72 |

FOREIGN PATENT DOCUMENTS

| | | |
|---|---|---|
| EP | 1 099 405 A1 | 5/2001 |
| JP | 01-113018 | 5/1989 |
| JP | 01-185239 | 7/1989 |
| JP | 01-280439 | 11/1989 |
| JP | 03-021186 | 1/1991 |
| JP | 6-335451 | 12/1994 |
| JP | 8-238216 | 9/1996 |
| JP | 10-201708 | 8/1998 |
| JP | 10-210324 | 8/1998 |
| JP | 11-099125 | 4/1999 |
| JP | 11-341485 | 12/1999 |
| JP | 2000-23183 | 1/2000 |
| JP | 2000-041942 | 2/2000 |
| JP | 2000-81577 | 3/2000 |
| JP | 2000-249935 | 9/2000 |
| JP | 2001-29313 | 2/2001 |
| JP | 2001-37718 | 3/2001 |
| JP | 2001-137183 | 5/2001 |
| JP | 2001-169300 | 6/2001 |
| WO | WO 00/69324 | 11/2000 |

* cited by examiner

*Primary Examiner*—Behrooz Senfi
(74) *Attorney, Agent, or Firm*—Scully, Scott, Murphy & Presser, P.C.

(57) ABSTRACT

An endoscopic image processing system processes an image signal produced by picking up the image of an intracavitary region of an object to be examined using an electronic endoscope. The endoscopic image processing system includes a detection unit that detects at least one of the type of electronic endoscope connected to the endoscopic image processing system, based on information inherent to the electronic endoscope, and the type of image pickup device incorporated in the connected electronic endoscope, and an image processing unit processes the image signal produced by the electronic endoscope according to the signal level of the image signal. A domain designation unit designates a first domain to be processed by the image processing unit within the image data according to the detected type of electronic endoscope.

15 Claims, 17 Drawing Sheets

FIG.8

```
FREEZE MENU
    FREEZE MODE
        PRE-FREEZE          4 (LEVEL)
        BLUR CORRECTION     ON
```

FIG.9

| | | |
|---|---|---|
| IHb DESIGNATION MENU | | |
| IHb | | |
| IHb AREA | ALL | |
| IHb RANGE | NORMAL | |
| IHb AVERAGE | OFF | (ENABLING OR DISABLING OF DISPLAY OF IHb AVERAGE DURING DISPLAY OF NORMAL IMAGE) |

FIG.16

FOR HIGH LUMINANCE

| COLOR ENHANCEMENT LEVEL | | DEGREE OF ENHANCEMENT (COEFFICIENT) | |
|---|---|---|---|
| | | PRESENT EMBODIMENT | RELATED ART |
| LOW | 1 | 1.0 | 1.0 |
| | ⟨ | ⟨ | ⟨ |
| | 4 | 1.0 | 1.0 |
| HIGH | 5 | 1.5 | 1.0 |
| | ⟨ | ⟨ | ⟨ |
| | 8 | 3.0 | 1.0 |

ENDOSCOPE IMAGE PROCESSING APPARATUS

CROSS-REFERENCE TO RELATED APPLICATION

The present application claims a priority from Japanese Patent Application No. 2002-70498 filed in Japan on Mar. 14, 2002, and Japanese Patent Application No. 2003-65561 filed in Japan on Mar. 11, 2003. The contents of the disclosures are cited in the description, claims, and drawings of the present applicant.

This application is the U.S. national phase of a 371 of PCT/JP03/03071, filed Mar. 14, 2003.

TECHNICAL FIELD

The present invention relates to an endoscopic image processing system that processes an image signal produced by an endoscope.

BACKGROUND ART

In recent years, endoscopes have been widely adopted in the field of medicine or the like. Aside from endoscopes that perform normal image processing, there are endoscopes that perform image processing to calculate hematic information concerning a region to be examined in an object to be examined.

For example, Japanese Unexamined Patent Application Publication No. 2001-37718 has disclosed an image processing system that performs image processing so as to quantitatively display a difference between a normal region and a lesion in an object to be examined for the purpose of assisting in diagnosis.

However, in this type of image processing system, if a different type of electronic endoscope is employed and, for example, a solid-state image pickup device incorporated in the endoscope offers a different number of pixels, it is hard to display an image using an appropriate domain within the number of pixels. In other words, time-consuming work is needed in order to designate a domain, which is used for display, according to the number of pixels offered by the solid-state image pickup device incorporated in the electronic endoscope to be employed actually. Consequently, it takes too much time for diagnosis.

Moreover, the image processing for calculating hematic information may be adopted in combination with other image processing. In this case, for example, a quasi image produced by performing the image processing for calculating hematic information may become different from a desired quasi image because of other image processing.

The present invention attempts to overcome the foregoing point. An object of the present invention is to provide an endoscopic image processing system that even when a different type of endoscope is employed, or more particularly, even when an image pickup device incorporated in an endoscope employed offers a different number of pixels, can display an image, which has undergone predetermined image processing, using an appropriate domain of pixels.

Another object of the present invention is to provide an endoscopic image processing system capable of preventing a change in an image, which has undergone predetermined image processing, because of other image processing that is adopted in combination.

DISCLOSURE OF INVENTION

An endoscopic image processing system in accordance with the present invention has constituent features described below.

An endoscopic image processing system that processes an image signal produced by picking up the image of an intracavitary region of an object to be examined using an electronic endoscope comprises: a detecting means that detects at least one of a type of electronic endoscope connected to the endoscopic image processing system on the basis of information inherent to the electronic endoscope and a type of image pickup device incorporated in the connected electronic endoscope; an image processing means that performs predetermined processing on an image signal produced by the electronic endoscope according to the signal level of the image signal; and a domain designating means that, when the detecting means detects the type of connected electronic endoscope on the basis of the information inherent to the electronic endoscope, designates a first domain to be processed by the image processing means within image data, which is carried by the image signal produced by the electronic endoscope, according to the detected type of electronic endoscope.

BRIEF DESCRIPTION OF THE DRAWINGS

FIG. 8 shows an example of a freeze designation menu screen image;

FIG. 9 shows an example of an IHb designation menu screen image;

FIG. 11 is a flowchart describing an example of actions to be performed for enabling calculation of IHb values and displaying an IHb average or the like;

FIG. 16 is an operational explanatory diagram concerning comparison with color enhancement performed according to a related art.

BEST MODE FOR CARRYING OUT THE INVENTION

Figure 1:
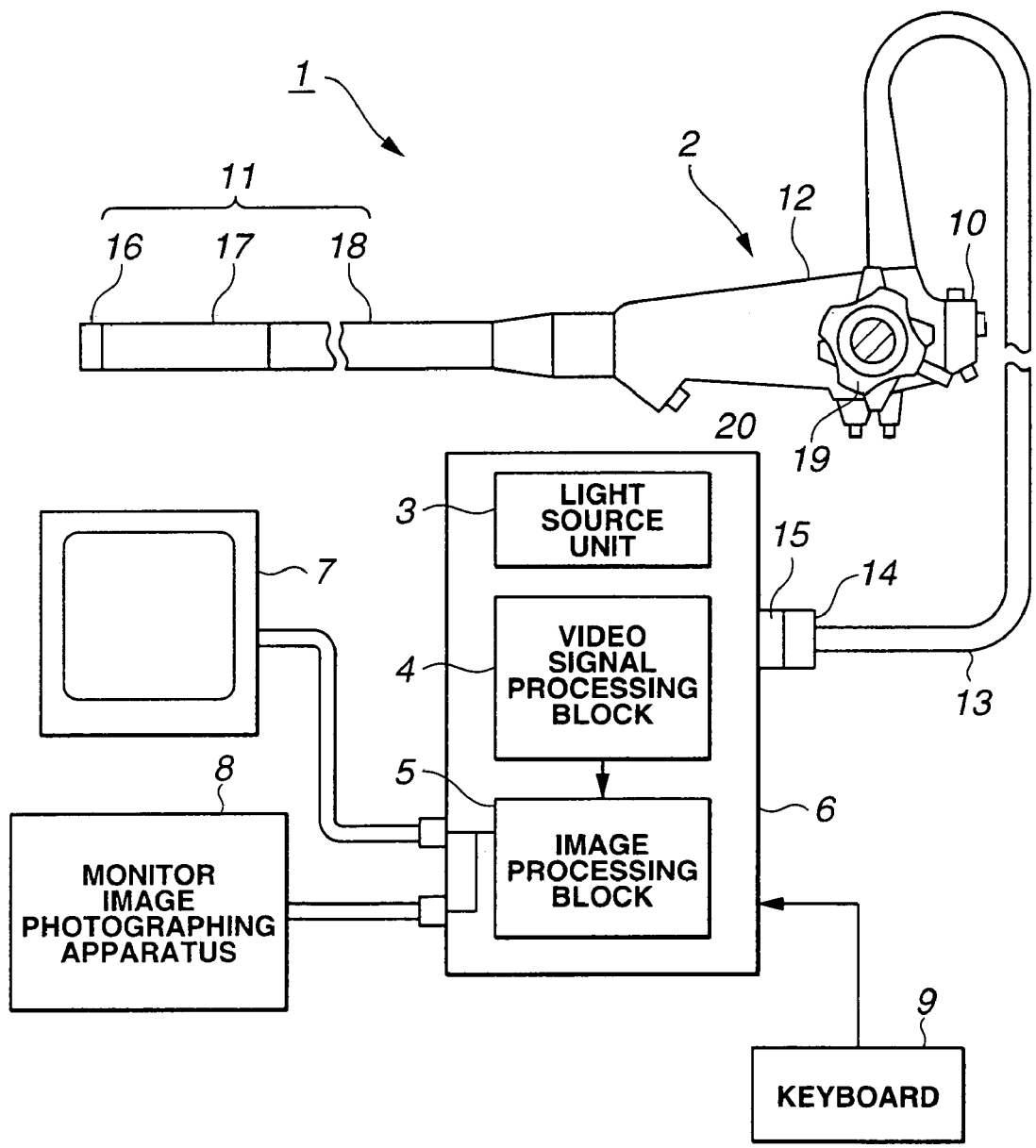
FIG. 1 shows the overall configuration of an endoscope system including a first embodiment of the present invention.

Referring to the drawings, embodiments of the present invention will be described below.

To begin with, a first embodiment of the present invention will be described.

Figure 2:
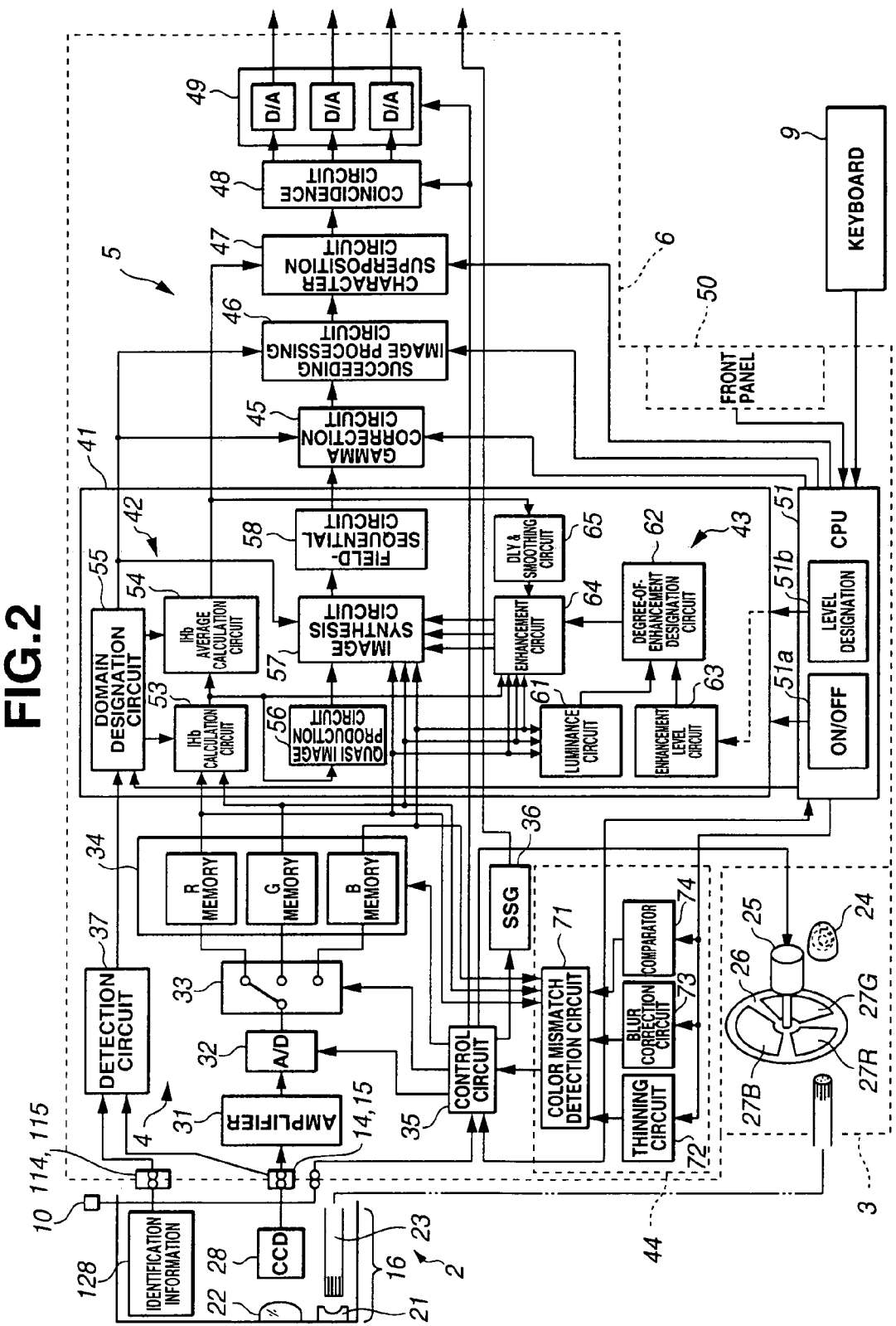
FIG. 2 is a block diagram showing the internal configuration of the endoscope system shown in FIG. 1.
Figure 3:
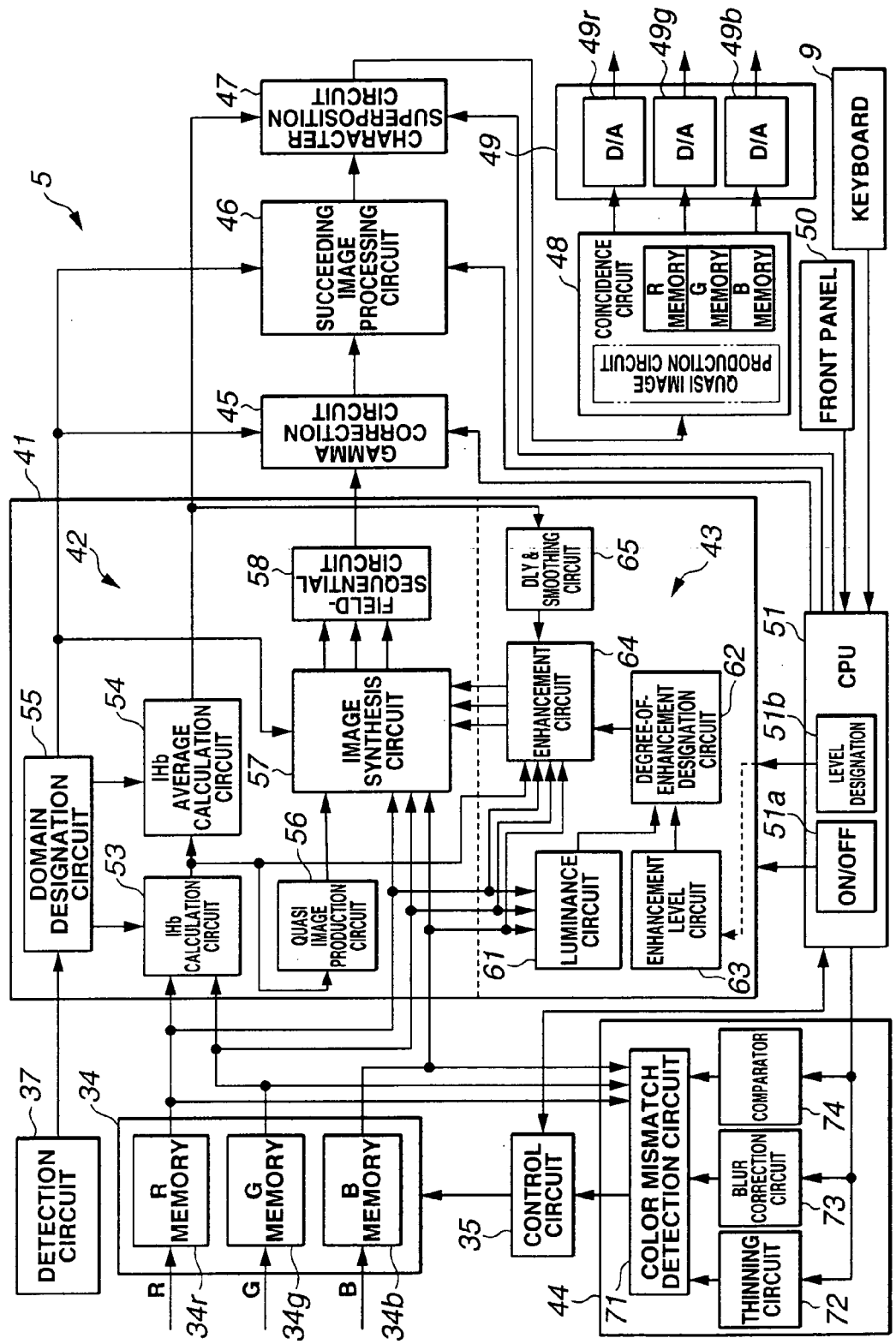
FIG. 3 is a block diagram showing the configuration of an image processing block.
Figure 4:
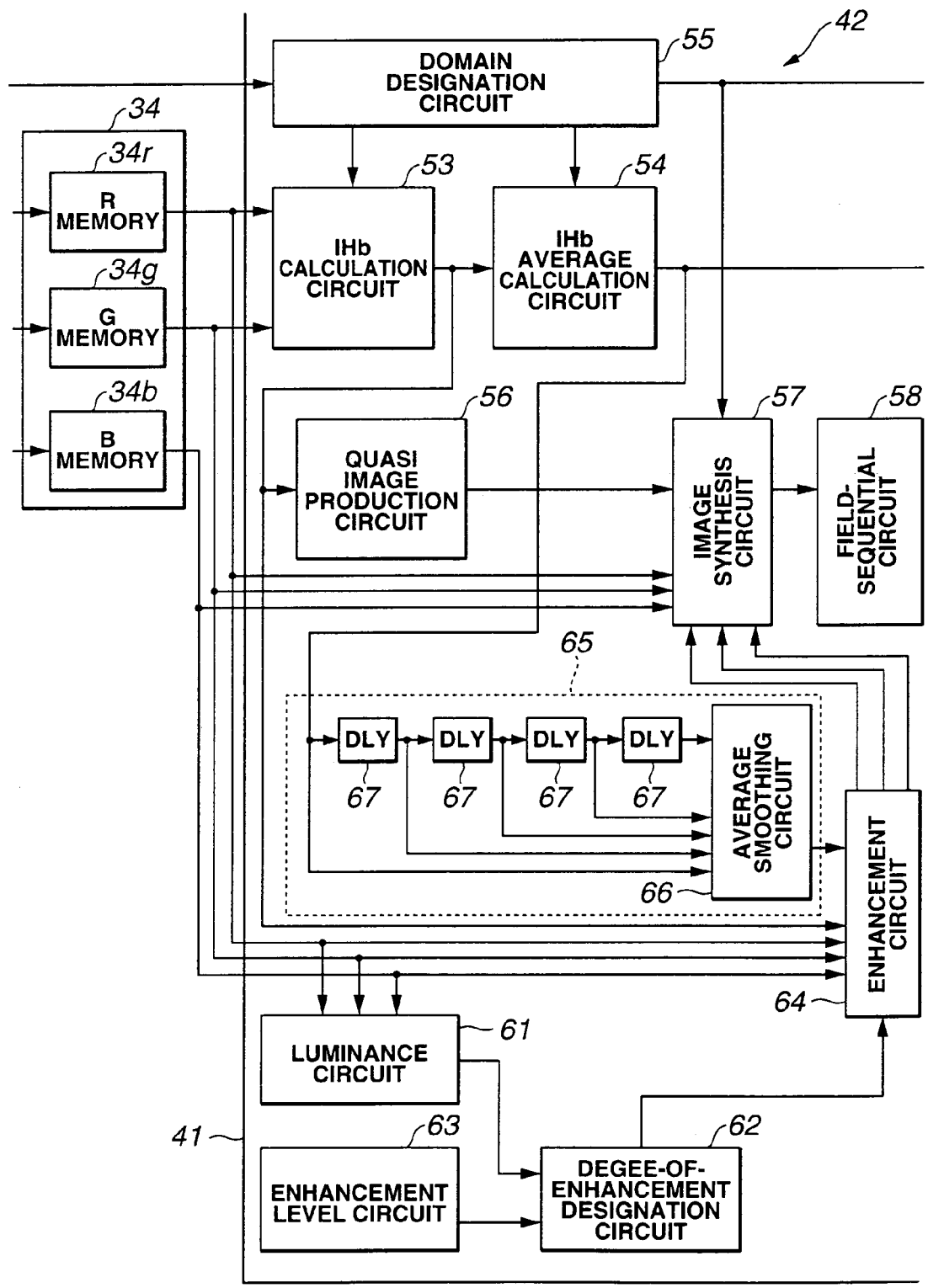
FIG. 4 is a block diagram showing the configuration of an IHb processing circuit.

FIG. 1 shows the overall configuration of an endoscope system including the first embodiment. FIG. 2 shows the internal configuration of the endoscope system. FIG. 3 shows the configuration of an image processing block. FIG. 4 shows the configuration of an IHb processing circuit. Herein, an IHb value is a value correlating to an amount of hemoglobin that is regarded as hematic information.

Figure 5A:
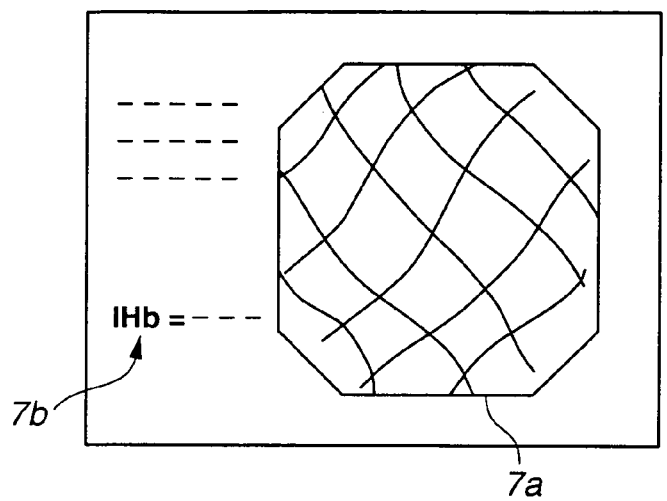
FIG. 5A shows an example of a normal image and a major quasi image displayed on a monitor.
Figure 5B:
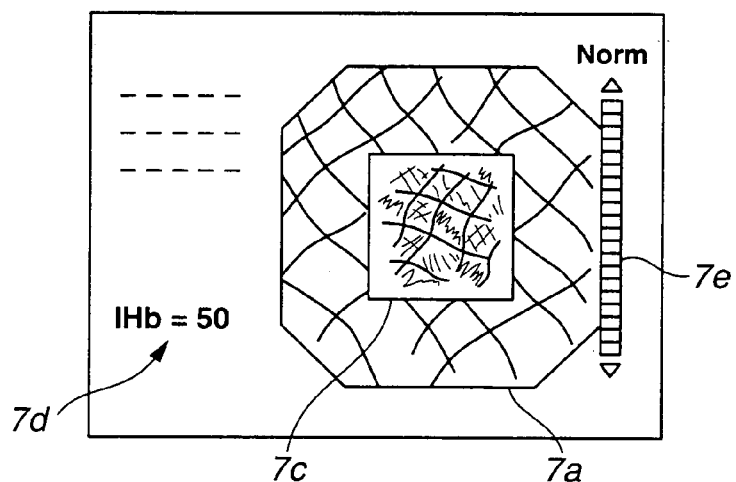
FIG. 5B shows another example of the normal image and major quasi image displayed on the monitor.
Figure 5C:
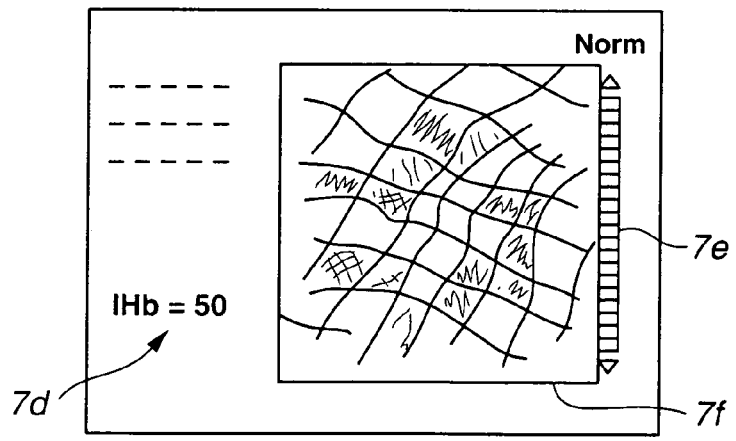
FIG. 5C shows still another example of the normal image and major quasi image displayed on the monitor.
Figure 6:
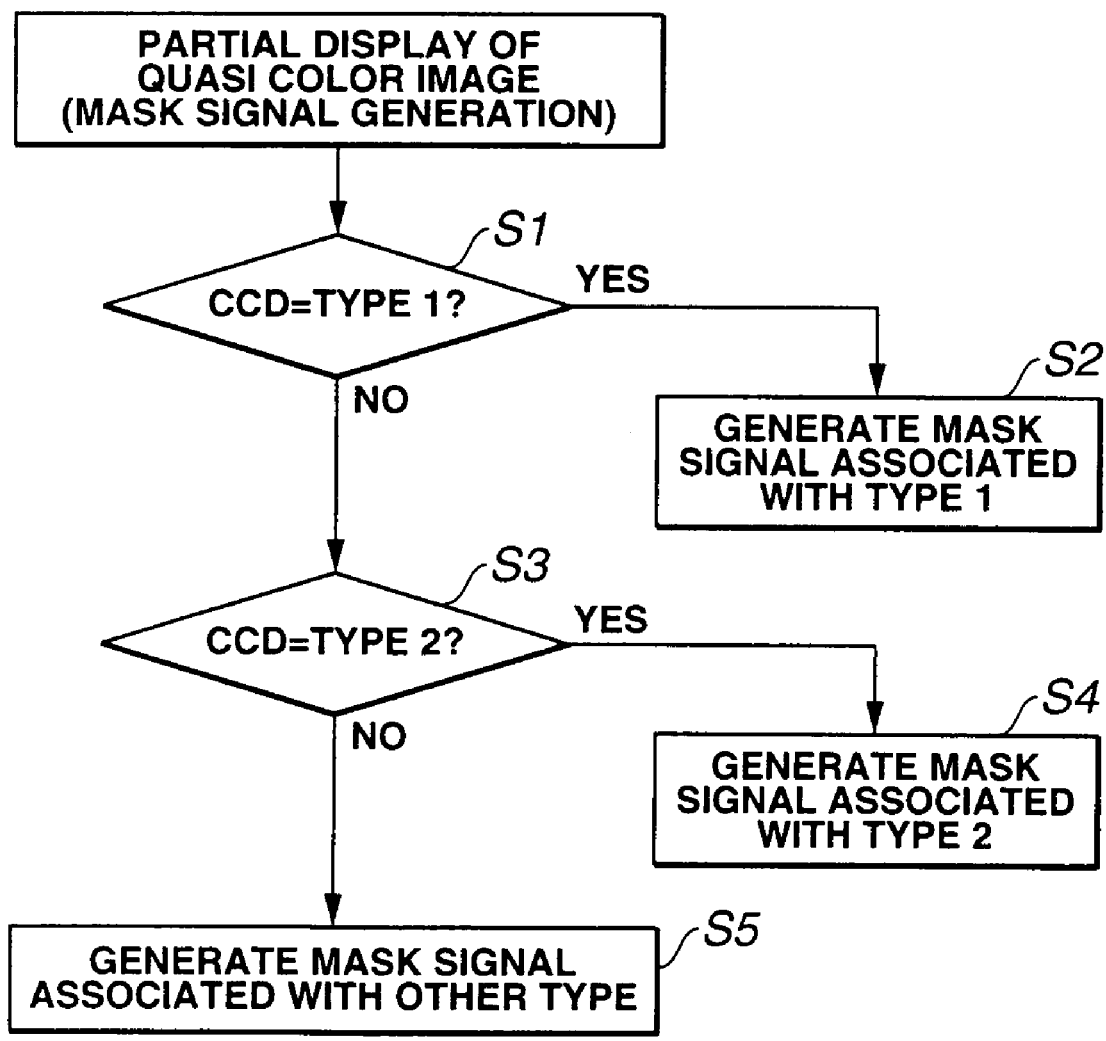
FIG. 6 is a flowchart describing actions to be performed for detecting a type of CCD and producing a mask signal associated with the type of CCD.
Figure 7:
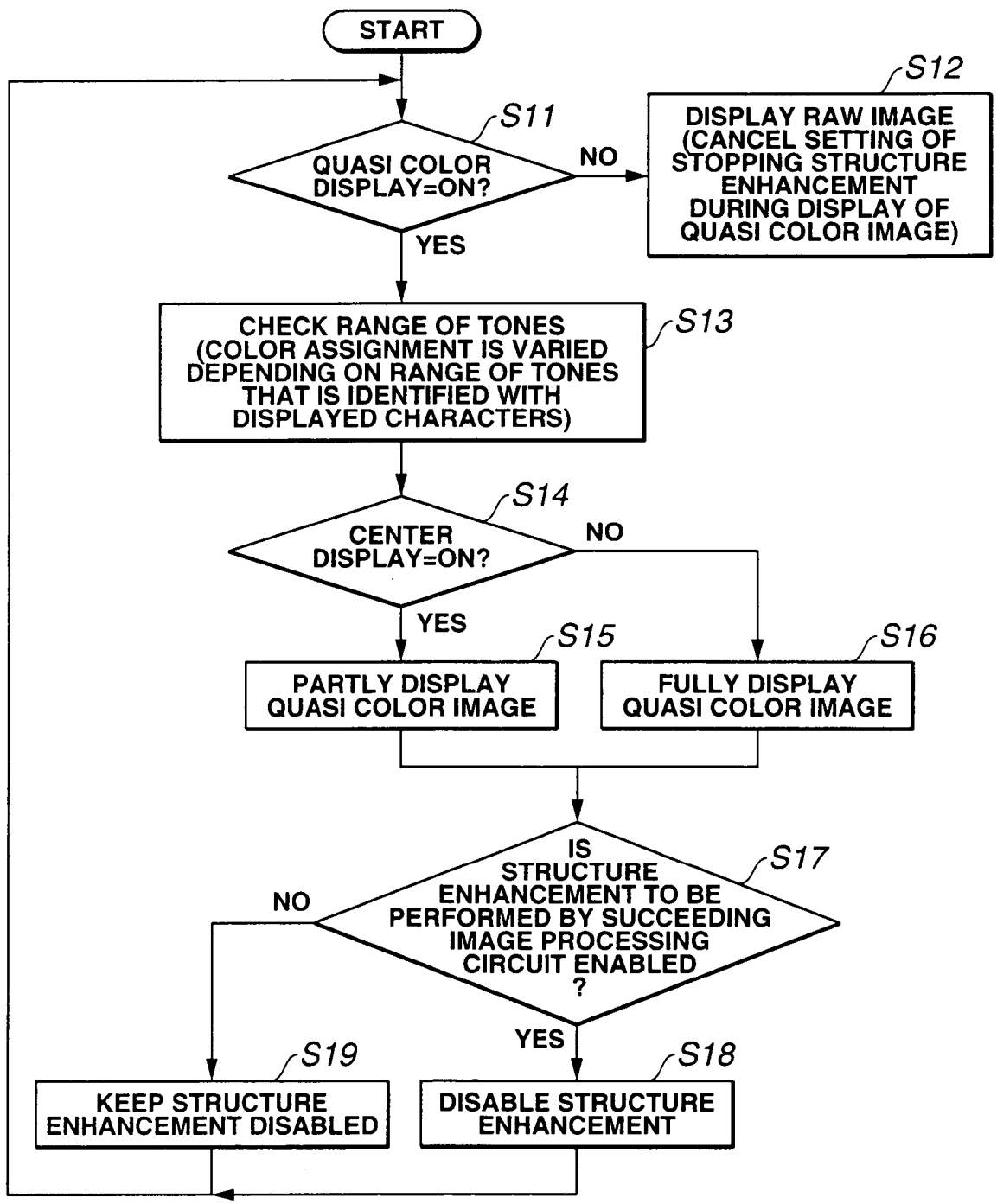
FIG. 7 is a flowchart describing typical actions to be performed for displaying a quasi color image.
Figure 10:
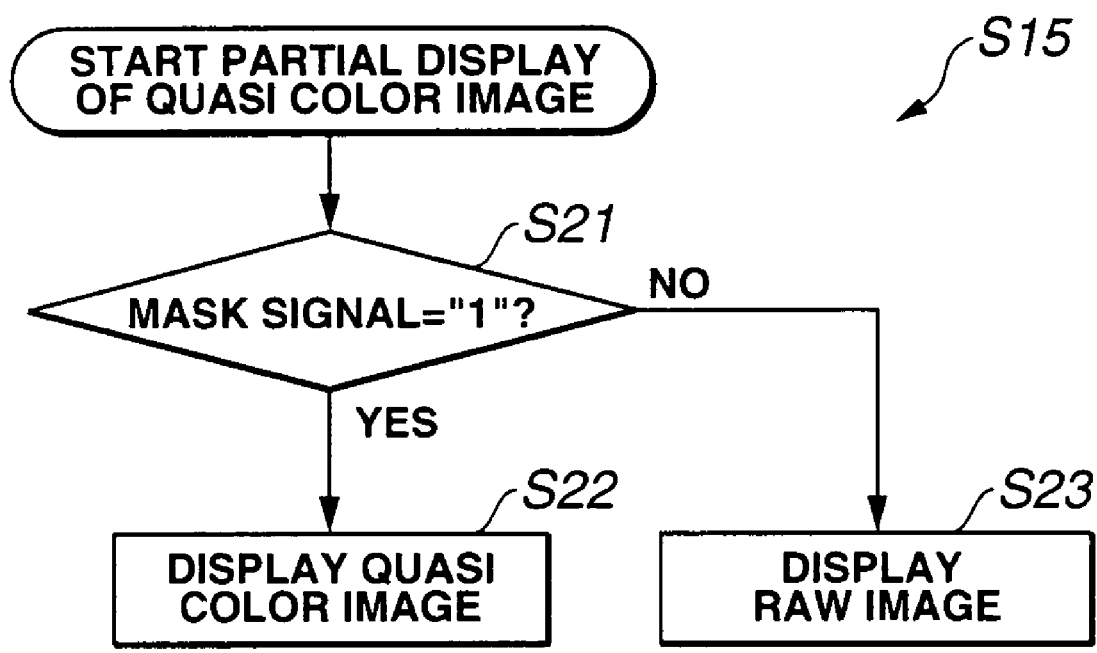
FIG. 10 is a flowchart describing actions to be performed for displaying a quasi color image.
Figure 11:
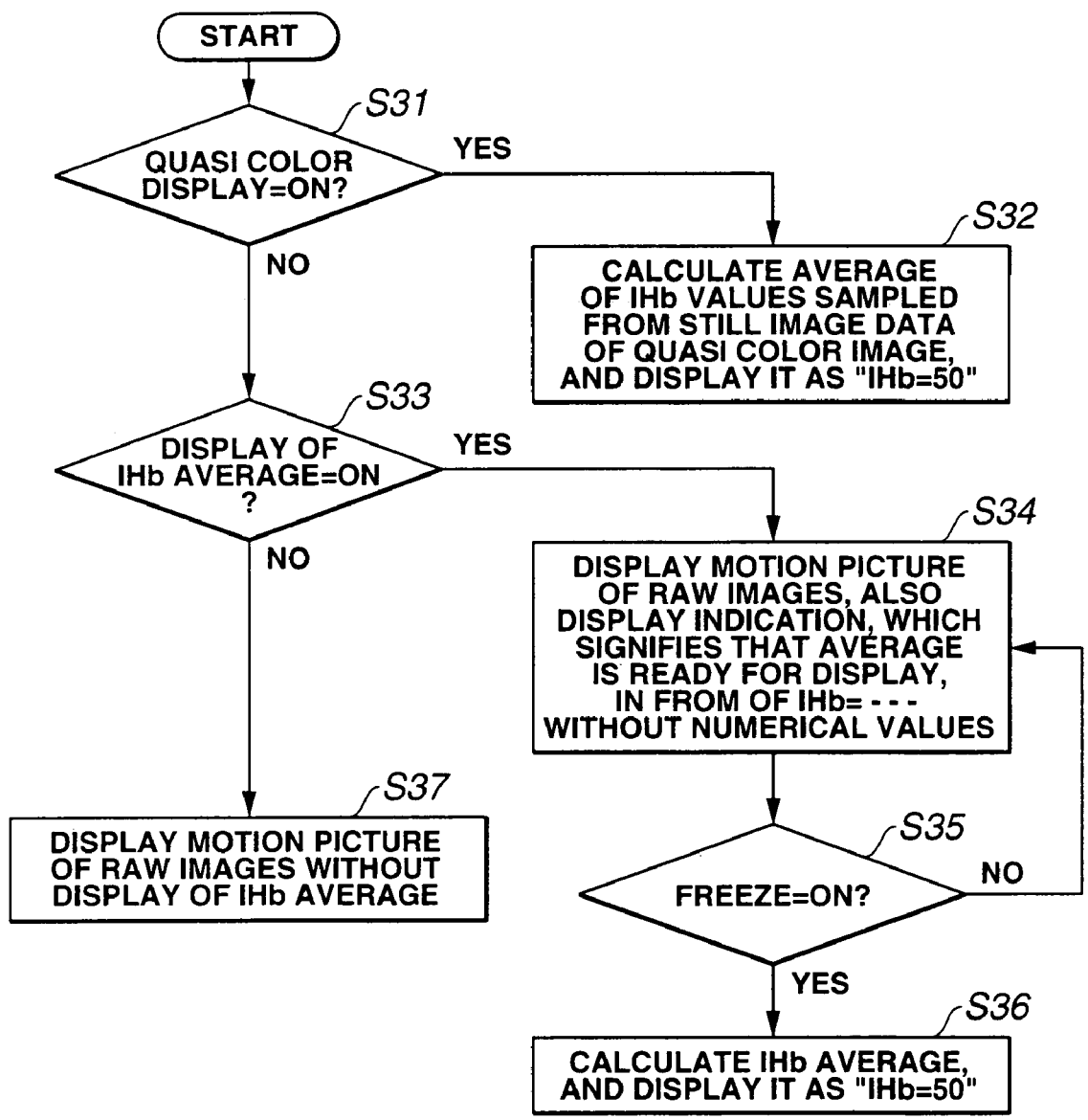
Figure 12A:
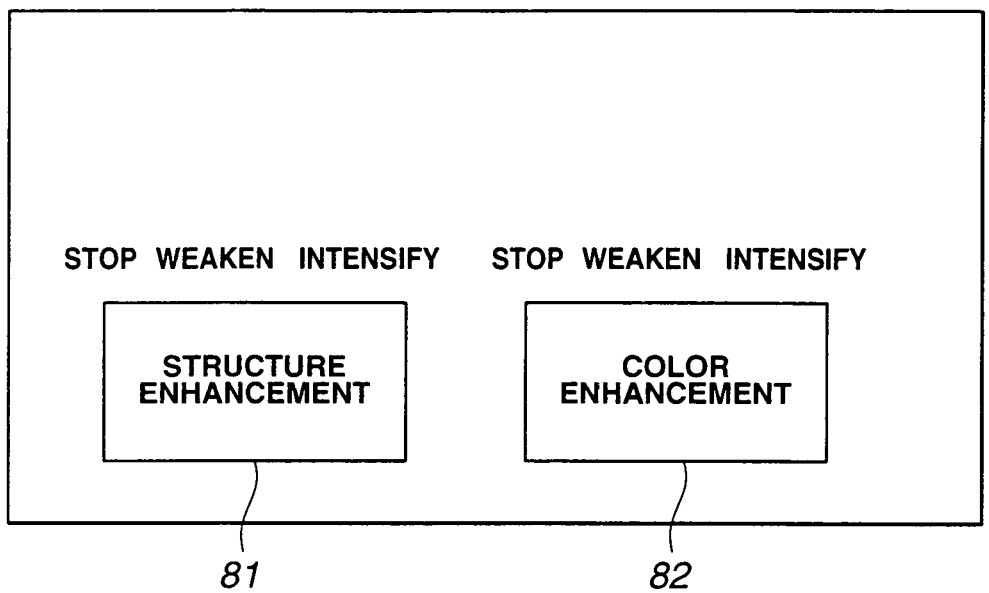
FIG. 12A shows an example of display signifying that structure enhancement and color enhancement are interlocked with each other.
Figure 12B:
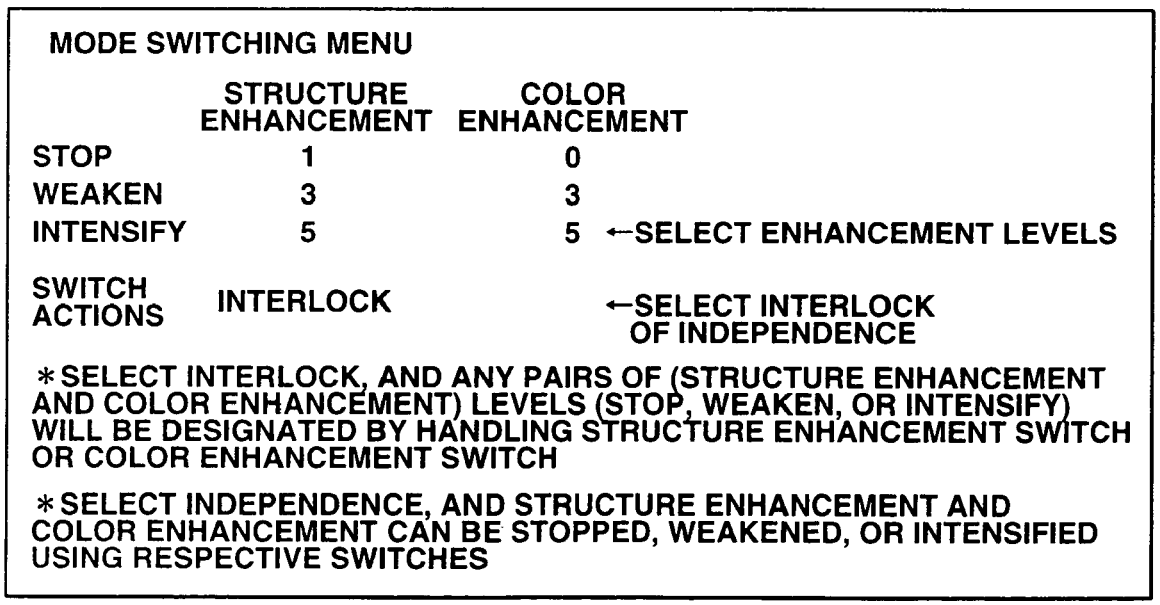
FIG. 12B shows an example of display signifying that structure enhancement and color enhancement are interlocked with each other.
Figure 13A:
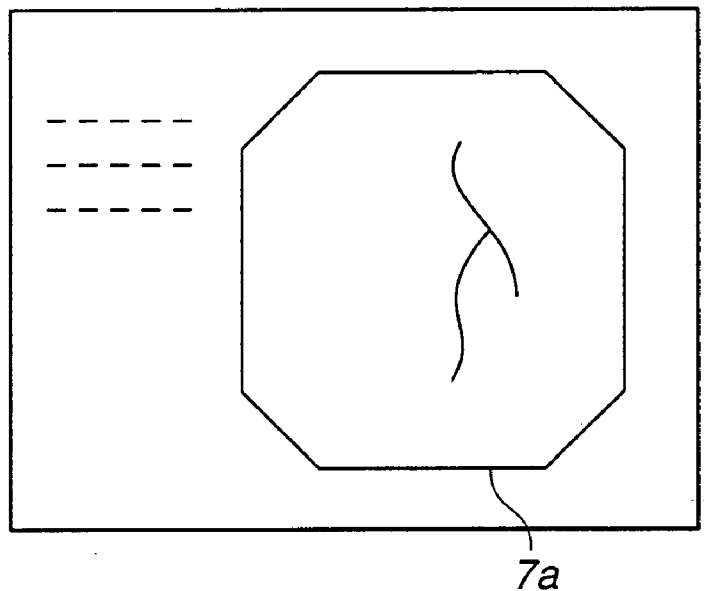
FIG. 13A shows an example of the display of an IHb average along with a change from a motion picture to a still image.
Figure 13B:
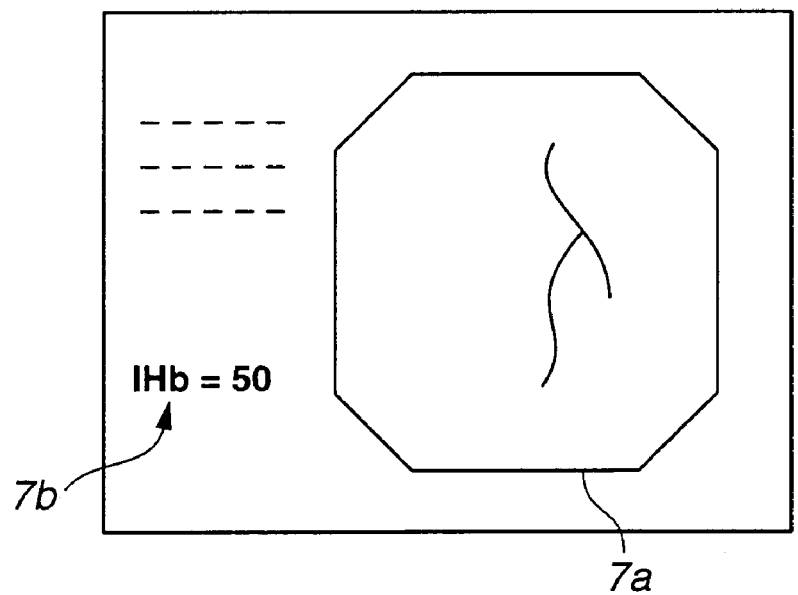
FIG. 13B shows an example of the display of an IHb average along with a change from a motion picture to a still image.

FIG. 5A, FIG. 5B, and FIG. 5C show examples of a normal image and a major quasi image displayed on a monitor. FIG. 6 describes actions to be performed for detecting a type of CCD and producing a mask signal associated with the type of CCD. FIG. 7 describes typical actions to be performed for displaying a quasi color image. FIG. 8 shows an example of a freeze designation menu screen image. FIG. 9 shows an example of an IHb designation menu screen image. FIG. 10 describes actions to be performed for displaying a quasi color image portion. FIG. 11 describes an example of actions to be performed for enabling IHb calculation and displaying an IHb average. FIG. 12A and FIG. 12B are explanatory diagrams signifying that structure enhancement and color enhancement are interlocked with each other. FIG. 13A and FIG. 13B are explanatory diagrams showing a screen on which an IHb average is displayed along with a change from a motion picture to a still image.

As shown in FIG. 1, an endoscope system 1 including the present embodiment comprises: an electronic endoscope 2 having an image pickup means; a light source unit 3 that supplies illumination light to the electronic endoscope 2; a video processor 6 in which a video signal processing block 4 that processes a video signal (image signal) produced by the image pickup means and an image processing block 5 that performs image processing on an output signal of the video signal processing block 4 are incorporated; a monitor 7 on which an image is displayed according to an image signal sent from the video processor 6; a monitor image photographing apparatus 8 that photographs a monitor image (endoscopic image) displayed on the monitor 7; and a keyboard 9 connected to the video processor 7 and used to transmit a directive signal that directs enabling or disabling of image processing or to enter patient data or the like.

The electronic endoscope 2 has an elongated and, for example, movable insertion unit 11. A large-diameter operation unit 12 is coupled to the rear end of the insertion unit 11. A flexible universal cord 13 is extended from the lateral side of the rear end of the operation unit 12. A connector 14 fixed to the end of the universal cord 13 is freely detachably attached to a connector receptacle 15 formed in the video processor 6.

The insertion unit 11 has a hard distal section 16, a bending section 17, which can be freely bent and adjoins the distal section 16, and an elongated flexible section 18, which has flexibility, concatenated in that order from the distal end thereof. Moreover, the bending section 17 can be bent in a rightward or leftward direction or in an upward or downward direction by turning an angulation knob 19 formed on the operation unit 12. Moreover, the operation unit 12 has an insertion port 20 that communicates with a treatment instrument channel running through the insertion unit 11.

Moreover, scope switches 10 including a freeze switch to be handled in order to direct freeze, and a release switch to be handled in order to direct exposure are located at the apex of the operation unit 12 of the electronic endoscope 2. When the scope switch 10 is handled in order to, for example, direct freeze, the directive signal is transferred to a control circuit 35 (see FIG. 2) incorporated in the video processor 6. The control circuit 35 controls a memory unit 34 (red, green, and blue memories 34r, 34g, and 34b included in the memory unit 34) (see FIG. 3) so that a frozen image will be displayed.

Moreover, the keyboard 9 or the front panel 50 of the video processor 6 (see FIG. 2) may be handled in order to direct freeze. Consequently, the directive signal is transmitted to the control circuit 35 via a CPU 51 (see FIG. 2). The control circuit 35 in turn extends control appropriately.

When the release switch is handled in order to direct exposure, a frozen image is displayed and a release signal is transmitted to the monitor image photographing apparatus 8. Consequently, the frozen image is photographed.

As shown in FIG. 2, an illumination lens 21 and an objective optical system 22 are locked in an illumination window and an observation window respectively that are formed in the distal section 16. A light guide 23 formed with a fiber bundle is disposed behind the illumination lens 21. The light guide 23 is passed through each of the insertion unit 11, operation unit 12, and universal cord 13, and fixed to the connector 14.

When the connector 14 is attached to the video processor 6, illumination light emanating from the light source unit 3 incorporated in the video processor 6 is propagated to the incident end of the light guide 23.

The light source unit 3 includes a lamp 24 and a rotary filter 26 located on the path of the illumination light emanating from the lamp 24 and rotated by a motor 25.

The lamp 24 emits visible light. The rotary filter 26 has color transmission filters 27R, 27R, and 27B, which transmit light rays belonging to mutually different regions of wavelengths arranged circumferentially. The characteristics of the color transmission filters 27R, 27G, and 27B of the rotary filter 26 are such that the color transmission filters will pass light rays belonging to the regions of wavelengths which determine red (R), green (G), and blue (B) respectively.

Light emanating from the lamp 24 has light components thereof, which belong to the respective regions of wavelengths, time-sequentially separated from one another by the rotary filter 26, and then falls on the incident end of the light guide 23. The illumination light is introduced into the distal section 16 by way of the light guide 23, and irradiated through the illumination lens 21 locked in the illumination window formed in the distal plane. Consequently, an object such as a region to be examined is illuminated with field-sequential illumination light including red, green, and blue light rays.

On the other hand, a solid-state image pickup device, for example, a charge-coupled device (CCD) 28 is located at the position of the image plane of the objective optical system 22. A subject image illuminated with the field-sequential illumination light is converged on the photoelectric conversion surface of the CCD 28 by means of the objective optical system 22, and converted into an electric signal by the CCD 28. An image (image pickup) signal resulting from photoelectric conversion performed by the CCD 28 is transferred to the video signal processing block 4, and then transferred to an amplifier 31 that amplifies the image signal up to a voltage falling within a predetermined range (for example, from 0 to 1 V).

An output signal of the amplifier 31 is converted into a digital signal by an A/D converter 32, and transferred to a selector 33 having one input terminal and three output terminals. Red, green, and blue signals transmitted time-sequentially are separated from one another by the selector 33, and transferred to the memory unit 34.

The red, green, and blue signals separated from one another are stored in the associated red, green, and blue memories 34r, 34g, and 34b (included in the memory unit 34) (see FIG. 3 and FIG. 4) (reference numerals 34r, 34g, and 34b are omitted from FIG. 2).

The control circuit 35 controls analog-to-digital conversion performed by the A/D converter 32, and storing (writing) or reading of color signals in or from the red, green, and blue memories 34r, 34g, and 34b included in the memory unit 34: Moreover, the control circuit 35 transmits a reference signal to a sync signal generation circuit (SSG in FIG. 2) 36. The sync signal generation circuit 36 generates a sync signal synchronous with the reference signal. When writing in the red, green, and blue memories 34r, 34g, and 34b is inhibited, a still image can be displayed (the same applies to red, green, and blue memories included in a coincidence circuit 48 that will be described later).

Moreover, according to the present embodiment, even when an electronic endoscope 2 having different endoscope-inherent identification information (128 in FIG. 2) is employed, a signal produced by the different type of electronic endoscope can be processed appropriately. Herein, the endoscope-inherent information includes, for example, optical type information representing an angle of view or a degree of optical zoom, usage information (indicating use for the superior digestive tract or use for the inferior directive tract), and information representing the number of pixels to be offered by the incorporated CCD 28. According to the present embodiment, the identification information 128 is detected using a connector 114, a connector receptacle 115, and a detection circuit 37.

An optimal example of a storage means in which the endoscope-inherent identification information 128 is stored is a memory means such as a RAM or ROM. Otherwise, a difference in the resistance of a resistive element may be adopted as inherent information.

According to the present embodiment, type information included in the identification information, such as, the number of pixels to be offered by the image pickup device (CCD 28) incorporated in the electronic endoscope 2 can be directly detected on the path of a signal sent from the CCD 28.

For example, the detection circuit 37 detects a difference in the number of pins included in the connector 14 via the connector receptacle 15 on the path of a signal sent from the CCD 28 to the succeeding amplifier. Thus, the type of CCD 28 incorporated in the electronic endoscope 2 actually connected to the video processor 6, which determines the number of pixels to be offered by the CCD 28, is detected. In other words, the type of CCD 28 determining the number of pixels to be offered by the CCD 28 is verified based on a difference in the number of pins included in the connector 14.

A means that detects the type of CCD 28 determining the number of pixels to be offered by the CCD 28 is not limited to the means that checks the number of pins included in the connector 14 which is associated with the type of CCD 28 determining the number of pixels to be offered by the CCD 28. Alternatively, a means that applies a CCD driving signal to the CCD, checking the number of peaks of the waveform of an output signal of the CCD, and thus detecting the number of pixels (number of horizontal dots, number of vertical dots) will do.

Red, green, and blue color signals read from the memories 34r, 34g, and 34b are transferred to an IHb processing block 41 that is included in the image processing block 5 and that calculates a value (hereinafter, IHb value) correlating to an amount of hemoglobin which is regarded as hematic information.

According to the present embodiment, the IHb processing block 41 includes: an IHb processing circuit 42 that performs quasi image production, that is, calculates an IHb value from each pixel, averages IHb values calculated from all pixels, and displays a quasi color image on the basis of the IHb values calculated from all the pixels; and a color enhancement circuit 43 that performs color enhancement.

The present embodiment also includes a color smear detection block 44 that detects color smear so that when a quasi color image based on IHb values is displayed in the form of a frozen image, the image can be displayed with little color smear.

A gamma correction circuit 45 performs gamma correction on a field-sequential signal transmitted from the IHb processing block 41. A succeeding image processing circuit 46 performs structure enhancement. Thereafter, a character superposition circuit 47 superposes patient data or a calculated IHb average on an image. Thereafter, a coincidence circuit 48 converts the field-sequential signal into coincident signals.

The coincidence circuit 48 includes, as shown in FIG. 3, red, green, and blue memories. The coincidence circuit 48 temporarily writes data items carried by the field-sequential signal in the red, green, and blue memories, and simultaneously reads the data items. The coincidence circuit 48 thus transmits coincident red, green, and blue signals.

The coincident red, green, and blue signals are transferred to three D/A converters 49r, 49g, and 49b included in a D/A conversion unit 49 (see FIG. 3) (reference numerals 49r, 49g, and 49b are omitted from FIG. 2). The signals are then converted into analog red, green, and blue signals, and transferred to each of the monitor 7 and monitor image photographing apparatus 8. Incidentally, the control circuit 35 controls writing or reading in or from the red, green, and blue memories included in the coincidence circuit 48, and D/A conversion performed by the D/A conversion unit 49.

The monitor image photographing apparatus 8 includes: a monitor which is not shown and on which, similarly to the monitor 7, an image or the like is displayed; and a photographing device (more particularly, a camera) that photographs an image or the like displayed on the monitor and thus records the image.

A user displays a normal image (also called a raw image), which is produced under normal visible illumination light, on the monitor 7. The user handles a switch on the front panel 50 of the video processor 6 or the keyboard 9 so as to direct display of an IHb image. The directive signal is transferred to a CPU 51. In response to the directive signal, the CPU 51 controls the IHb processing block 41 or the like.

The configuration of the IHb processing block 41 will be described below. As shown in FIG. 2 and FIG. 3, a red signal read from the red memory 34r and a green signal read from the green memory 34g are transferred to an IHb calculation circuit 53 included in the IHb processing block 41. IHb values are then calculated, and transmitted to an IHb average calculation circuit 54 that averages IHb values.

Moreover, information of the type of CCD detected by the detection circuit 37 is transferred to a domain designation circuit 55. The domain designation circuit 55 designates a domain, which is used for display, for a quasi image according to the information of the type of CCD so that when a quasi image is displayed, the quasi image will be displayed in an appropriate size.

The information of the domain designated by the domain designation circuit 55 is transmitted to each of the IHb calculation circuit 53 and IHb average calculation circuit 54. IHb values are calculated from the domain.

The IHb calculation circuit 53 performs arithmetic operations expressed with formula (1) below so as to calculate an IHb value from each pixel.

$$IHb = 32 \times \text{Log } 2(R/G) \qquad (1)$$

where R denotes red image data, and G denotes green image data.

It is easy to implement the arithmetic operations expressed with formula (1) in circuits. For example, a divider that is not shown is used to perform an arithmetic operation on received red image data and green image data. The resultant output of the divider is converted using a logarithmic conversion table that is not shown and formed with a ROM or the like. Moreover, a CPU or the like may be used to perform the arithmetic operations expressed with formula (1).

IHb values calculated by the IHb calculation circuit 53 are transmitted to the IHb average calculation circuit 54. The IHb average calculation circuit 54 averages received IHb values on the basis of the number of pixels belonging to the domain designated by the domain designation circuit 55, and thus works out an IHb average.

The IHb values calculated by the IHb calculation circuit 53 are also transferred to a quasi image production circuit 56. The quasi image production circuit 56 produces a quasi image, which is displayed in quasi colors, on the basis of the IHb values, and transmits the quasi image to an image synthesis circuit 57 that performs image synthesis.

The image synthesis circuit 57 receives quasi image data produced by the quasi image production circuit 56, and red, green, and blue image data items read from the red, green, and blue memories 34r, 34g, and 34b. The image synthesis circuit 57 synthesizes the received image data items according to a mask signal sent from the domain designation circuit 55, and transmits synthetic image data to a field-sequential circuit 58 that converts the image data into a field-sequential signal.

More particularly, the image synthesis circuit 57 transmits red, green, and blue image data items, which represent a raw image, during a period during which the mask signal assumes logical 0, and transmits quasi image data during a period during which the mask signal assumes logical 1. The image synthesis circuit 57 thus transmits synthetic image data to the field-sequential circuit 58 on the succeeding stage.

The field-sequential circuit 58 field-sequentially transmits the red, green, and blue components of the synthetic image data. Specifically, the field-sequential circuit 58 field-sequentially transmits the red, green, and blue image data items to the gamma correction circuit 45.

According to the present embodiment, information concerning the domain designated by the domain designation circuit 57 (specifically, the mask signal) is transmitted to each of the gamma correction circuit 45 and succeeding image processing circuit 46. As described in relation to a second embodiment, gamma correction or structure enhancement can be performed on raw image data surrounding a predetermined domain via the CPU 51 according to a user's choice. (According to the first embodiment, information of the domain designated by the domain designation circuit 57 need not always be transmitted to each of the gamma correction circuit 45 and succeeding image processing circuit 46.)

Moreover, an IHb average calculated by the IHb average calculation circuit 54 is transmitted to the character superposition circuit 47. The calculated IHb average can be displayed on a monitor screen. Even in this case, a user can select display or non-display via the CPU 51.

Moreover, red, green, and blue image data items read from the red, green, and blue memories 34r, 34g, and 34b are transferred to a luminance circuit 61 included in the color enhancement circuit 43. A luminance signal is then produced and transferred to a degree-of-enhancement designation circuit 62 that designates a degree of enhancement.

Moreover, the degree-of-enhancement designation circuit 62 receives an enhancement level designated by an enhancement level circuit 63 that designates an enhancement level. A degree of enhancement is determined based on the level of the received luminance signal and the received enhancement level, and transmitted to an enhancement circuit 64 that performs enhancement according to the degree of enhancement.

The enhancement circuit 64 receives red, green, and blue image data items read from the red, green, and blue memories 34r, 34g, and 34b, and IHb values calculated by the IHb calculation circuit 53. Moreover, the enhancement circuit 64 receives an IHb average calculated by the IHb average calculation circuit 54 via a delay and smoothing circuit (DLY & smoothing in FIG. 2 and FIG. 3) 65.

The enhancement circuit 64 performs color enhancement on the received red, green, and blue image data items, and transmits the resultant data items to the image synthesis circuit 57. When color enhancement is enabled, the image synthesis circuit 57 synthesizes quasi color data with color-enhanced image data but not with raw image data. Needless to say, when quasi color display is stopped, only a color-enhanced image sent from the enhancement circuit 64 may be transmitted. Otherwise, a synthetic image of a raw image and a color-enhanced image rather than a synthetic image of a raw image and a quasi color image may be transmitted.

The color-enhanced-image data includes color-enhanced red, green, and blue image data items produced based on IHb values, an IHb average, luminance levels, and an enhancement level.

Moreover, when a raw image is synthesized with a color-enhanced image but not with a quasi color image, a domain within the raw image data that is supposed to be synthesized with quasi color data is synthesized with color-enhanced image data. When full display is designated instead of partial display, a color-enhanced image is fully displayed.

FIG. 4 shows the details of the delay and smoothing circuit 65 shown in FIG. 2 and FIG. 3.

An IHb average calculated by the IHb average calculation circuit 54 is transferred directly (without delay) to an average smoothing circuit 66. IHb average signals that are delayed by one field, two fields, three fields, and four fields respectively by means of four delay elements (DLYs) 67 are transferred to the average smoothing circuit 66.

IHb average signals sampled over five fields by the four delay elements 67 are averaged, and a resultant IHb average signal is smoothed and transmitted to the enhancement circuit 64. In other words, an IHb average signal detected over a plurality of fields is smoothed in order to minimize great variations of the IHb average signal occurring on each field. Display optimal to observation is thus attained.

A user displays a normal image (also called a raw image) produced under normal visible illumination light on the monitor 7. Otherwise, the user handles a directive switch on the front panel 50 of the video processor 6 or the keyboard 9 so as to direct display of an IHb image. The directive signal is transferred to the CPU 51, and the CPU 51 controls the IHb processing block 41 in response to the directive signal.

In this case, the user handles the switch on the front panel 50 or the keyboard 9 so as to direct enabling or disabling of display of an IHb image (quasi image) or enabling or disabling of color enhancement. In response to the directive, the CPU 51 controls enabling or disabling (ON/OFF) 51a. Moreover, when designation of an enhancement level is directed, the CPU 51 controls level designation 51b which an enhancement level circuit 63 performs to designate an enhancement level.

Moreover, red, green, and blue image data items read from the red, green, and blue memories 34r, 34g, and 34b are transferred to a color smear detection circuit 71 included in the color smear detection block 44. A degree of color smear is detected by detecting a degree of correlation between each pair of red, green, and blue image data items.

If freeze of an image is directed, an image suffering the least color smear is detected. A signal is then transmitted to the control circuit 35 so that the image having the least color smear thereof detected over a field will be displayed. The control circuit 35 inhibits writing in the red, green, and blue memories 34r, 34g, and 34b included in the memory unit 34, and changes an image to be displayed on the monitor 7 serving as a display means and an image to be displayed on the monitor included in the monitor image photographing apparatus 8 into still images.

As a method of detecting a degree of color smear in an image to be frozen, any of three color smear detection methods to be described below or a combination thereof is adopted. Thus, an image suffering the least color smear is detected.

Specifically, the color smear detection circuit 71 uses a thinning circuit 72, a blur correction circuit 73, or a comparator 74 to detect color smear.

If a large number of images must be checked to see if they suffer color smear, the thinning circuit 72 is used to thin out the number of time-sequential images. Images resulting from thinning are checked to see if they suffer color smear. Thus, a large number of images can be checked.

Using the comparator 74, two methods are conceivable. One of the methods uses a multi-stage comparator to compare changes in a plurality of images sampled over fields with one another at a time so as to search an image suffering the least color smear. (This method has the demerits that the scale of a circuit becomes large and the number of images that can be dealt with is limited, but has the merit that since fast processing is possible, an image suffering the least color smear can be searched for a short period of time.) The other method is such that two of a plurality of images sampled over fields are compared with each other in order to search an image suffering the least color smear. (This method has the merits that the scale of a circuit is small and the number of images that can be dealt with is larger than that to be dealt with by the multi-stage comparator, but has the demerit that since fast processing is impossible, it takes much time to search an image suffering the least color smear.)

Moreover, according to an image constructing method, the display positions of red, green, and blue image components of the thus detected image suffering the least color smear are shifted two-dimensionally in units of several pixels. Thus, an image whose color smear is further reduced is constructed. This method, that is, blur correction is implemented in a blur correction circuit 73.

According to the above method, since the red, green, and blue images are displaced, the edges of the images are invalidated. This results in a small view image, but has the merit of further reducing color smear.

A menu is used to select any of the foregoing methods or to designate a combination thereof in advance, or the foregoing methods may be switched based on settings. FIG. 8 shows an example of a freeze menu. The menu has an item of pre-freeze in which a numerical value is designated as a freeze level.

For example, the numerical value entered as a level corresponds to the number of images that can be dealt with. If the numerical value is, for example, 8 indicating the highest level, since 8 is equal to or larger than the limit of the number of images that can be dealt with through multi-stage comparison, the method of comparing two of images each other is adopted. If the level is lower than level 8, it means that the number of images to be dealt with is smaller than the limit of the number of images capable of being dealt with through multi-stage comparison. Therefore, multi-stage comparison is adopted in order to detect color smear.

If On is specified in an item of blur correction in the menu shown in FIG. 8, blur correction is performed on an image that suffers the least color smear and that is detected according to any of the aforesaid methods. Consequently, an image whose color smear is further reduced can be constructed.

According to the present embodiment, the detection circuit 37 detects, for example, the type of CCD 28 incorporated actually in the electronic endoscope 2 which determines the number of pixels offered by the CCD 28. A domain to be used for display is designated for a quasi image according to the number of pixels determined with the detected type of CCD. Consequently, even when a different type of electronic endoscope 2 is connected for use, a quasi image is automatically displayed in an appropriate size.

To be more specific, in a normal operational state, endoscopic images are, as shown in FIG. 5A, displayed in the form of a motion picture in an octagonal endoscopic image display area 7a on the display surface of the monitor 7. Moreover, patient data as well as an indication that an IHb average is ready for display is displayed by the left side of the endoscopic image display area 7a.

Specifically, IHb=--- (7b) is displayed, signifying that an IHb average is ready for display. The indication that an IHb average is ready for display may not be displayed if a user selects non-display. Incidentally, the IHb average helps distinguish a lesion from a sound region (normal region).

When display of a quasi color image is enabled, a quasi color image is, for example, as shown in FIG. 5B, displayed in a mask area 7c in the center of the endoscopic image display area 7a. In this case, an IHb average can be displayed (7d) instead of the indication that an IHb average is ready for display.

In other words, a quasi color image is displayed in the mask area 7c that corresponds to the center of an endoscopic image depicting a region of interest in an object to be observed. A raw image is displayed around the mask area 7c.

In this case, a color bar 7e indicating a range of tones employed in a quasi color image is displayed by the right side of the endoscopic image display area 7a. In FIG. 5B, the color bar indicates a normal range of tones.

In the present embodiment, when a quasi color image is, as shown in FIG. 5B, displayed only in the mask area 7c in the center of the endoscopic image display area 7a (that is, when a quasi color image is partly displayed), the domain designation circuit 55 generates a mask signal according to a process described in FIG. 6. Therefore, even when the CCD 28 offers a different number of pixels, a quasi color image is partly displayed in an appropriate size.

In other words, when a quasi color image is partly displayed, the domain designation circuit 53 judges from a detection signal sent from the detection circuit 37 at step S1 described in FIG. 6 whether the CCD 28 actually employed is of type 1. If the CCD 28 is of type 1, a mask signal associated with type 1 is generated at step S2. The mask signal is then transmitted to the image synthesis circuit 57.

The mask signal associated with type 1 is a binary signal that assumes logical 1 at the timing of partly displaying a quasi color image, and that assumes logical 0 during the other period. Based on the mask signal, the image synthesis circuit 57 performs image synthesis to partly fit a quasi color image in a raw image, and transmits the resultant image to the succeeding stage. Consequently, the quasi color image is, as shown in FIG. 5B, partly displayed on the display surface of the monitor 7.

On the other hand, if it is found at step S1 described in FIG. 6 that the CCD is not of type 1, control is passed to step S3. It is then judged whether the CCD 28 is of type 2. If it is judged that the CCD 28 is of type 2, the domain designation circuit 53 generates a mask signal associated with type 2 at step S4. The mask signal is then transmitted to the image synthesis circuit 57. Even in this case, a quasi color image is, similarly to the one shown in FIG. 5B, partly displayed.

On the other hand, when the condition presented at step S3 is not met, control is passed to step S5. A mask signal associated with other type is generated. Thus, even when a plurality of types of CCD 28 is usable, a quasi color image can be partly displayed in a size that is appropriate relative to the number of pixels offered by the CCD 28 (without, unlike the related art, the necessity of the work of designating a domain according to the number of pixels).

A description will be made by taking a concrete example. For example, when the CCD 28 is of type 1, the number of pixels offered by the CCD 28 corresponds to a product of 400 by 400. While a domain including the same number of pixels as a product of 200 by 200 (a quarter size) and being located in the center of the square matrix of 400 pixels is being dealt with, a binary mask signal to be generated assumes logical 1. During the other period, the mask signal assumes logical 0. Moreover, when the CCD 28 is of type 2, the number of pixels offered by the CCD 28 corresponds to a product of 800 by 600. In this case, while a domain including the same number of pixels as a product of 400 by 300 (a quarter size) and being located in the center of the matrix of 800 pixels by 600 pixels is being dealt with, a binary mask signal to be generated assumes logical 1. During the other period, the mask signal assumes logical 0.

Whichever of the CCD of type 1 or type 2 is employed, a quasi color image is partly displayed in the center of a raw image in a quarter display size.

The present embodiment supports not only a display mode in which a quasi color image is, as shown in FIG. 5B, partly displayed but also a display mode in which a quasi color image is, as shown in FIG. 5C, fully displayed (7f). When a user selects (enables) (partial) display of a quasi color image in the center, the quasi color image is, as shown in FIG. 5B, partly displayed. When the display in the center is not selected, a quasi color image is, as shown in FIG. 5C, fully displayed. Incidentally, the full display 7f of a quasi color image shown in FIG. 5C may be made in an octagonal area as shown in FIG. 5A.

A description has been made of a case where the CCD 28 incorporated in an endoscope employed offers a different number of pixels. The present embodiment is not limited to this case. As mentioned above, the type of endoscope employed may be verified based on any other factor, and settings may be determined so that image processing will be performed optimally to the employed endoscope.

Specifically, when it is detected based on identification information 128 (see FIG. 2) that an endoscope whose optical factor such as an angle of view or a degree of optical zoom is different is employed, settings are determined so that an image will be partly displayed in an appropriate size. For example, when an endoscope including an optical zoom feature is employed, an image produced by an image pickup device has a significant meaning as a whole. The size of partial display is set to a large value. On the other hand, when an endoscope including no optical zoom feature is employed, the size is set to a small value.

Moreover, when an endoscope for examining the inferior digestive tract that is used to observe the large intestine is employed, unlike when an endoscope for examining the superior digestive tract that is used to observe the stomach is employed, since the inferior digestive tract has many lumens, regions to be observed are relatively dark. Therefore, the display size is set to a large value so that image processing can be performed appropriately.

Next, a process of displaying a distribution of IHb values in quasi colors with the endoscope system 1 brought to an operational state will be described with reference to FIG. 7.

The power supply of the endoscope system 1 is turned on and the endoscope system 1 is brought to an operational state. The CPU 51 incorporated in the video processor 6 monitors the entry of a directive at the keyboard 9 or the like. The CPU 51 judges at step S11 whether a directive of enabling quasi color display has been entered.

If quasi color display is not enabled, a raw image is displayed at step S12. Endoscopic images are displayed in the form of a motion picture on the display surface of the monitor 7 in the state shown, for example, in FIG. 5A.

According to the present embodiment, when a raw image is displayed, structure enhancement to be performed by the succeeding image processing circuit 46 is enabled in order to display a structure-enhanced image. Moreover, when quasi color display is enabled, structure enhancement is automatically stopped as described later for fear the tones employed in quasi color display may be changed.

Consequently, after quasi color display is enabled, if the quasi color display is stopped, the setting of stopping structure enhancement during display of a quasi color image is canceled. A raw image is displayed with structure enhancement enabled.

On the other hand, if it is judged at step S1 that quasi color display is enabled, the CPU 51 checks a range of tones at step S13. Specifically, the CPU 51 checks color assignment for quasi color display to see if a normal range of tones or a wide range of tones is adopted. The CPU 51 then controls display of a color bar indicating the color assignment of the normal or wide range of tones. The CPU 51 then judges at step S14 whether center display is stared (or designated).

If center display is designated, the CPU 51 controls the domain designation circuit 55 so that a domain designation signal will be transmitted to the image synthesis circuit 57. The image synthesis circuit 57 synthesizes a quasi image produced by the quasi image production circuit 56 with a raw image, and partly displays quasi colors at step S15. Control is then passed to step S17. Consequently, a quasi color image is partly displayed in the center of the raw image displayed in the endoscopic image display area 7a as shown in, for example, FIG. 5B. The color bar is displayed by the right side of the endoscopic image display area 7a.

On the other hand, if center display is not designated, a quasi color image is fully displayed at step S16. Control is then passed to step S17. Consequently, a quasi color image is, for example, as shown in FIG. 5C, fully displayed in a size nearly identical to the side of the endoscopic image display area 7a. (As mentioned above, although FIG. 5C shows a quasi color image displayed in a square area, the quasi color image may be displayed in an octagonal area like the endoscopic image display area 7a by cutting the four corners of the square area.) The color bar is displayed by the right side of the quasi color image.

FIG. 9 shows an IHb designation menu screen image. As shown in FIG. 9, the IHb designation menu includes an item in which an area in which an image based on IHb values is displayed, an item in which a range of tones assigned for quasi color display based on IHb values is designated, an item in which whether an IHb average is displayed during display of a normal motion picture is designated. In FIG. 9, the area in which an image based on IHb values is displayed is set to a full screen, the range of tones is set to the normal range of tones, and the display of an average is stopped.

After a quasi color image is partly displayed or fully displayed, it is judged at step S17 whether structure enhancement to be performed by the succeeding image processing circuit 46 is enabled. If structure enhancement is enabled, structure enhancement is stopped. Control is then returned to step S11.

On the other hand, if structure enhancement is not enabled, structure enhancement is kept stopped and control is returned to step S11.

As mentioned above, when a quasi color image is to be partly displayed or fully displayed, structure enhancement is automatically stopped. A quasi color image is then partly displayed or fully displayed. If a quasi color image based on IHb values is displayed, a change in quasi color display caused by structure enhancement can be efficiently prevented.

FIG. 10 describes the details of partial display of a quasi color image at step S15.

When partial display of a quasi color image is enabled, it is judged at step S21 whether the mask signal assumes logical 1. If so, a quasi color image is displayed at step S22. At this time, the quasi color image is displayed with image processing to be performed on the succeeding stage, or more particularly, gamma correction stopped. The quasi color image is, as shown in FIG. 5B, displayed in the center of the endoscopic image display area 7a.

On the other hand, if the mask signal does not assume logical 1 (period), a raw image is displayed at step S23. At this time, the raw image is displayed with image processing to be performed on the succeeding stage, or more particularly, gamma correction enabled. Consequently, the raw image is, as shown in FIG. 5B, displayed in the peripheral part of the endoscopic image display area 7a other than the center part thereof.

Next, a process of displaying an IHb average will be described with reference to FIG. 11.

At step S31, the CPU 51 judges whether quasi color display is enabled. If quasi color display is enabled, a quasi color image is displayed in the form of a still image at step S32. An average of IHb values sampled from the still image data is calculated and displayed in the form of "IHb=50." Herein, 50 is the IHb average calculated using the still image data of the quasi color image.

Specifically, in FIG. 11, quasi color display and still image display are interlocked with each other. If still image display is not interlocked with quasi color display, an IHb average is displayed together with a motion picture of quasi color images.

On the other hand, if quasi color display is not enabled, control is passed to step S33. It is then judged whether display of an IHb average is enabled. If the display of an IHb average is enabled, a motion picture of raw images and an indication that an average is ready for display are displayed at step S34. Specifically, the indication that an average is ready for display is "IHb=---" with no numerals displayed.

Moreover, even if quasi color display is enabled, if display of an IHb average is stopped, an IHb average may not be displayed.

At the next step S35, it is judged whether freeze is enabled. If freeze is enabled, IHb values are calculated, and an IHb average is displayed in the form of "IHb=50." If freeze is not enabled, control is returned to step S34.

If it is judged at step S33 that average display is not enabled, control is passed to step S37. A motion picture of raw images is displayed but an IHb average is not displayed (a motion picture of raw images is displayed without display of an IHb average).

The present embodiment supports an interlock mode in which a structure enhancement switch and a color enhancement switch on the front panel 51 are interlocked with each other.

Specifically, as shown in FIG. 12A, a structure enhancement switch 81 and a color enhancement switch 82 are handled in order to stop, weaken, or intensify structure enhancement and color enhancement.

A mode switching menu shown in FIG. 12B is supported in order to relieve a user of the labor of determining the structure enhancement level and color enhancement level. Namely, structure enhancement and color enhancement can be interlocked with each other with major structure and color enhancement levels associated with each other. If an interlock mode in which the switches are interlocked with each other is selected rather than an independent mode in which the switches are independent of each other, the structure enhancement switch 81 and color enhancement switch 82 are interlocked with each other.

In this mode, when one of the structure enhancement switch 81 and color enhancement switch 82 is handled, the other switch changes its contacts while being interlocked with the switch. In the present embodiment, when the interlock mode in which the switches are interlocked with each other is selected, designation of major structure and color enhancement levels and stop of structure and color enhancement can be performed readily.

The present embodiment provides advantages described below.

Even when a different type of electronic endoscope 2 is adopted, the type of CCD 28 is detected, and an image is produced based on IHb values and displayed in quasi colors. In this case, the quasi color image is displayed in the center of an image display area in an appropriate display size, or more particularly, in a substantially quarter size. An operator need not adjust the display size with labor. An IHb quasi color image can be displayed in the center of a raw image.

This results in an image processing system and an endoscope system capable of producing the quasi color image that helps quantitatively evaluate a difference between a normal region and a lesion of an object to be examined, and permitting easy observation.

Moreover, according to the present embodiment, not only an IHb quasi color image can be displayed in the center of a raw image in an appropriate display size but also the IHb quasi color image can be fully displayed. In other words, when an operator desires that the IHb quasi color image should be displayed over a wide part of the screen, the desire can be coped with.

Moreover, according to the present embodiment, when display of an IHb quasi color image is directed, the IHb quasi color image is displayed in the form of a still image. Since the IHb quasi color image does not change, diagnosis can be achieved readily.

Moreover, according to the present embodiment, when an IHb quasi color image is displayed, structure enhancement to be performed on the succeeding stage is automatically stopped. A change in the displayed IHb quasi color image caused by structure enhancement can be prevented.

Moreover, when display of a quasi color image is stopped, structure enhancement is re-enabled. A user need not perform the work of enabling structure enhancement. Thus, a user-friendly image processing system is realized with improved maneuverability.

Moreover, color enhancement can be performed and the resultant image can be displayed. Intensification of color breakup or halation can be prevented by properly determining the color enhancement level, or noise can be suppressed. This results in a naturally enhanced image that does not hinder viewing of a motion picture.

Moreover, structure enhancement and color enhancement can be interlocked with each other or made independent of each other according to a user's choice. This results in a user-friendly endoscope system.

According to the above description, in the partial display of a quasi color image, the quasi color image is displayed in the center of the endoscopic image display area 7a in a substantially quarter screen size. The display position and screen size may be able to be changed at, for example, the keyboard 9. Moreover, a frozen still image may be changed to other still image stored in a memory at the keyboard 9.

Moreover, structure enhancement to be performed by the succeeding image processing circuit 46 has been described. Electronic zoom or any other processing may be able to be performed.

According to the above description, a motion picture is displayed as shown in FIG. 5A. Alternatively, the indication signifying that an IHb average is ready for display may not be, as shown in FIG. 13A, displayed according to a user's choice. Moreover, when a still image is displayed, an IHb average may be, as shown in FIG. 13B, displayed together with the still image.

According to the first embodiment, a quasi image produced by the quasi image production circuit 56 is converted into a field-sequential signal at the field-sequential circuit 58, and transmitted to the succeeding stage. The quasi image production circuit 56 may be included in the coincidence circuit 48 as indicated with an alternate long and two short dashes line in FIG. 3 but not in the IHb processing block 41 indicated with a solid line in FIG. 3. Thus, the quasi color image may be produced.

In the above configuration, occurrence of color smear in a quasi color image can be minimized.

Next, a second embodiment of the present invention will be described with reference to FIG. 14. According to the first embodiment, when a quasi color image is partly displayed or fully displayed, structure enhancement to be performed on the succeeding stage is automatically disabled. According to the second embodiment, when a quasi color image is partly displayed, the succeeding image processing circuit 46 enables, as described in FIG. 14, structure enhancement relative a peripheral raw image portion.

Figure 14:
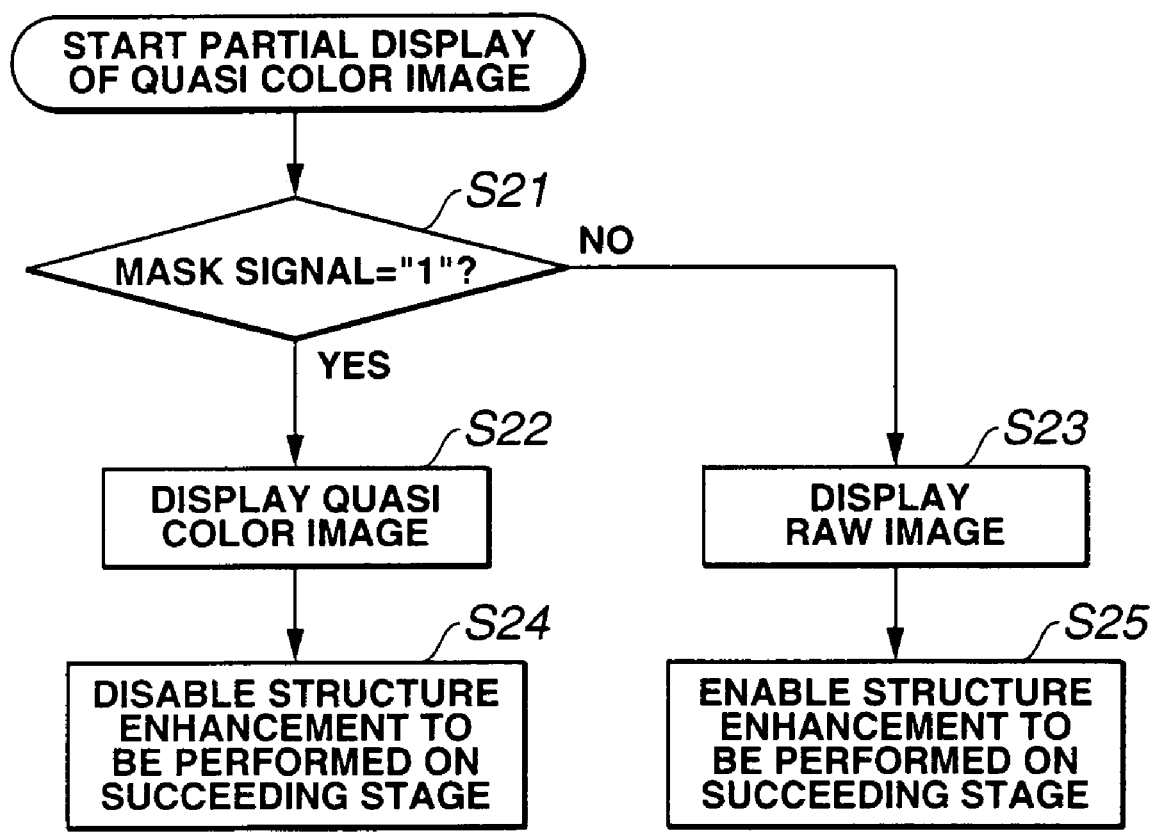
FIG. 14 is a flowchart describing an example of actions to be performed for displaying a quasi color image portion according to a second embodiment of the present invention.

Specifically, as described in FIG. 14, when a quasi color image is partly displayed, it is judged at step S21 whether the mask signal assumes logical 1 (as described in FIG. 10). If so, a quasi color image is displayed at step S22. At the next step S24, structure enhancement to be performed by the succeeding image processing circuit 46 is disabled.

On the other hand, if the mask signal does not assume logical 1 (period), a raw image is displayed at step S23. At the next step S25, structure enhancement to be performed by the succeeding image processing circuit 46 is enabled. Namely, structure enhancement is enabled relative to the raw image serving as a peripheral image.

According to the present embodiment, structure enhancement is not performed on an image portion displayed in quasi colors. Similarly to the first embodiment, the tones employed in the image portion displayed in quasi colors can be prevented from varying due to structure enhancement. Moreover, structure enhancement is performed on a raw image in order to clarify a depicted structure.

Figure 15:
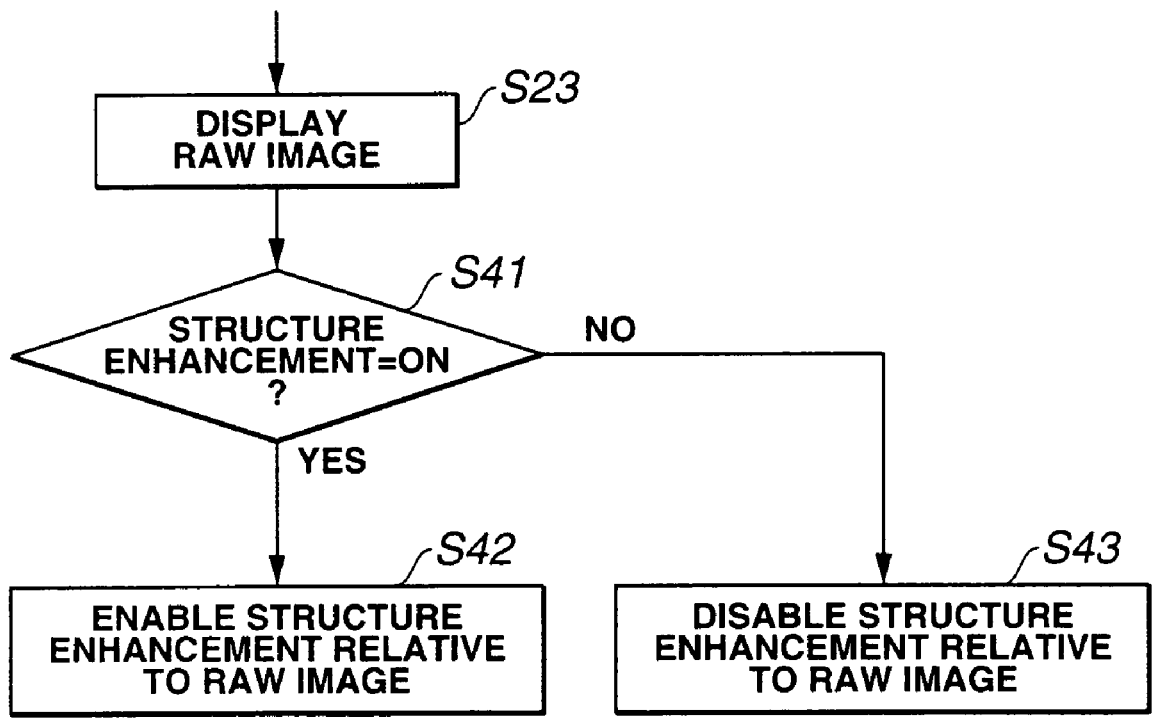
FIG. 15 is a flowchart describing an example of actions to be performed for displaying a quasi color image portion according to a variant.

Aside from the processing described in FIG. 14, a variant described in FIG. 15 may be adopted. Specifically, after step S23 described in FIG. 14 is completed, it is judged at step S41 in FIG. 15 whether structure enhancement is enabled. If structure enhancement is enabled, structure enhancement is performed on a raw image at step S42. If structure enhancement is disabled, structure enhancement is not performed at step S43.

In this case, a raw image can be displayed according to a user's choice. In other words, the number of options can be increased. For a quasi color image, structure enhancement can be selected as described in FIG. 15. Structure enhancement may be able to be enabled or disabled based on the result of selection.

The above description has been made in relation to structure enhancement to be performed by the succeeding image processing circuit 46. Alternatively, enabling or disabling of gamma correction to be performed by the gamma correction circuit 45 may be able to be selected. Specifically, as far as the first embodiment is concerned, gamma correction may be disabled along with quasi color display, and may be enabled along with display of a raw image.

As long as the second embodiment is concerned, when a quasi color image is displayed according to the process described in FIG. 14, gamma correction is disabled. When a raw image is displayed, gamma correction is enabled. According to the process described in FIG. 15, gamma correction is enabled or disabled according to the setting of enabling or disabling (on or off) of gamma correction.

Moreover, according to the present embodiment, once color enhancement is enabled, a degree of color enhancement can be varied depending on a luminance level according to whether a designated enhancement level is equal to or higher than a certain level, or lower than it.

FIG. 16 indicates the above mechanism. FIG. 16 presents the effectiveness in color enhancement in accordance with the present embodiment, and also presents the effectiveness therein in accordance with a related art for comparison.

As seen from FIG. 16, according to the related art, when luminance is high, even if a color enhancement level is set to a large value (needless to say when it is set to a small value), color enhancement is controlled not to be performed.

According to the present embodiment, when the color enhancement level is set to a large value, even if luminance is high, the color enhancement level is changed to a small value. Color enhancement is then carried out.

When the color enhancement level is set to a small value, similarly to the related art, color enhancement is not carried out.

Figure 17:
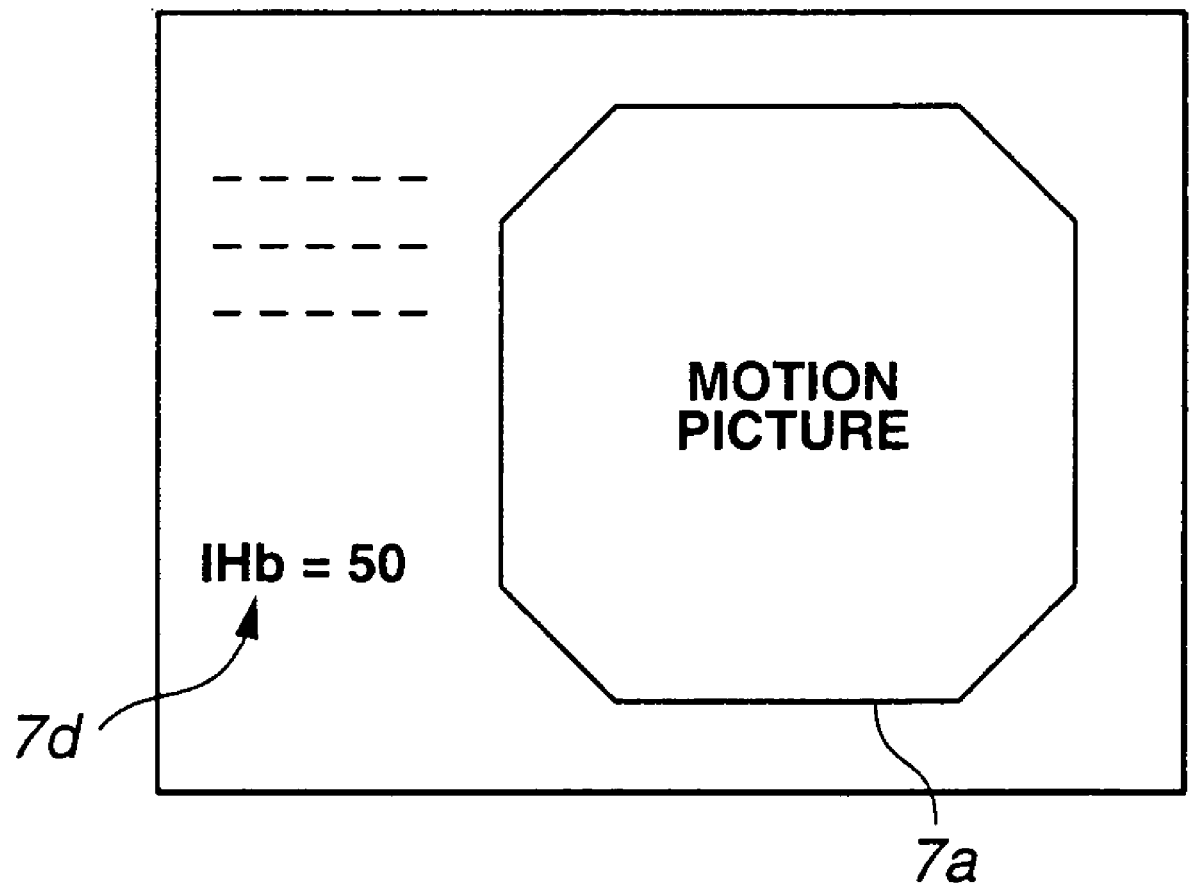
FIG. 17 shows a screen on which an IHb average is displayed while a motion picture is being displayed.

Moreover, according to the present embodiment, even when a motion picture is displayed, an IHb average may be, as shown in FIG. 17, displayed if a user selects so. Thus, the number of options is increased.

As mentioned above, the present embodiment provides nearly the same advantages as the first embodiment does. Moreover, processing associated with a user-designated option can be carried out.

Incidentally, an endoscope with a built-in solid-state image pickup device is not limited to an endoscope having the CCD 28 incorporated in the distal section of the insertion unit thereof. Alternatively, an electronic endoscope may be realized by mounting a TV camera on an optical endoscope that has the CCD 28 incorporated in an eyepiece unit thereof.

Moreover, the aforesaid embodiments have been described on the assumption that an image processing device which performs predetermined image processing to deal with a bloodstream is incorporated in a normal image processing apparatus (specifically, a video processor) which performs normal image processing (video processing) so that an image identical to a view falling on naked eyes can be displayed. Alternatively, the image processing device may be separated from the normal image processing apparatus.

According to the above description, the number of pixels offered by the CCD 28 dependent on the type of CCD 28 is detected. Alternatively, the pixel size of image data transmitted to the image processing device may be detected. A domain to be used for display may be designated for a processed image produced by the image processing device according to the detected pixel size, so that the processed image will be displayed in an appropriate display size.

Incidentally, a combination of parts of the aforesaid embodiments will belong to the present invention.

Japanese Unexamined Patent Application Publication No. 2001-37718 has disclosed an image diagnosis system in which a method of quantitatively displaying a difference between a normal region and a lesion of an object to be examined can be readily implemented.

When predetermined image processing is performed in order to deal with hematic information (IHb values) for the purpose of displaying the hematic information in quasi colors, if another image processing, for example, structure enhancement is performed on the succeeding stage, a color other than assigned colors may be generated. This varies the IHb quasi color display and results in an improper image. For the purpose of producing a proper view image, a solving means described below is conceivable.

An endoscopic image processing system for producing a signal that represents an endoscopic image of the interior of an object to be examined comprises:

an image processing means that performs predetermined image processing to deal with hematic information concerning the object to be examined according to the signal level of the endoscopic image signal;

a detecting means that detects at least one of the type of electronic endoscope connected to the endoscopic image processing system, which is detected based on information inherent to the electronic endoscope, and the type of image pickup device incorporated in the connected electronic endoscope; and a domain designating means that designates a predetermined domain, which is used for display, for a processed image produced by the image processing means according to the type of image pickup device detected by the detecting means.

The endoscopic image processing system further comprises:

a second image processing means that performs second image processing, which is different from the predetermined image processing that deals with the hematic information, on the succeeding stage; and a control means that when the processed image having undergone at least the predetermined image processing is displayed, disables the image pickup processing to be performed on the processed image by the second image processing means.

Enabling or disabling of the image processing which the second image processing means performs on an image other than the processed image having undergone the predetermined image processing can be selected.

Moreover, Japanese Unexamined Patent Application Publication No. 6-335451 describes image enhancement that is performed by utilizing IHb values. If an image suffers color smear or a change in luminance, an IHb average calculated for each field may greatly vary from field to field. In this case, an enhanced image based on IHb average is terribly affected to become improper for viewing.

For the purpose of realizing display optimal to viewing, a solving means described below is conceivable.

An endoscopic image processing system that produces a signal representing an endoscopic image of the interior of an object to be examined comprises:

an image processing means that performs predetermined image processing to deal with hematic information concerning the object to be examined according to the signal level of the endoscopic image signal;

a detecting means that detects at least one of the type of electronic endoscope connected to the endoscopic image processing system, which is detected based on information inherent to the electronic endoscope, and the type of image pickup device incorporated in the connected electronic endoscope; and a domain designating means that designates a predetermined domain, which is used for display for a processed image produced by the image processing means according to the type of image pickup device detected by the detecting means.

The endoscopic image processing system further comprises:

an average displaying means that displays an average of values based on which the processed image is produced; and a smoothing means that smoothens the average over a plurality of fields.

Japanese Unexamined Patent Application Publication No. 10-210324 has disclosed a related art according to which a naturally enhanced image that does not hinder viewing of a motion picture can be produced as an enhanced (color-enhanced) image based on IHb values with intensification of color breakup or halation prevented and enhancement of noise suppressed.

However, when the luminance in an image gets high, enhancement is suppressed uniformly irrespective of an enhancement level in order to prevent intensification of halation.

For the purpose of overcoming (alleviating) the above drawback, a solving means described below is conceivable.

An endoscopic image processing system that produces a signal representing an endoscopic image of the interior of an object to be examined comprises:

an image processing means that performs predetermined image processing to deal with hematic information concerning an object to be examined according to the signal level of the endoscopic image signal;

a detecting means that detects at least one of the type of electronic endoscope connected to the endoscopic image processing system, which is detected based on information inherent to the electronic endoscope, and the type of image pickup device incorporated in the connected electronic endoscope; and a domain designating means that designates a predetermined domain, which is used for display, for a processed image produced by the image processing means according to the type of image pickup device detected by the detecting means.

The endoscopic image processing system further comprises a color enhancing means that performs color enhancement.

The color enhancing means includes: a luminance detecting means that detects a luminance level; and an enhancement level designating means that designates an enhancement level. Depending on whether a designated enhancement level is equal to or larger than a certain value, or smaller than the certain value, the limit of a degree of enhancement to be designated by a degree-of-enhancement designating means realized by the luminance detecting means is varied.

The embodiments of the present invention have been described so far. The present invention is not limited to the embodiments but can be modified in various aspects without a departure from the spirit of the present invention.

INDUSTRIAL APPLICABILITY

As described so far, according to the present invention, there is provided an endoscopic image processing system that when a different type of endoscope is employed, or in particular, when an image pickup device incorporated in the endoscope employed offers a different number of pixels, can display an image produced by performing predetermined image processing on an appropriate domain.

Moreover, there is provided an endoscopic image processing system that even when other image processing is used in combination, can prevent an image having undergone predetermined image processing from changing.

The invention claimed is:

1. An endoscopic image processing system that processes an image signal produced by picking up the image of an intracavitary region of an object to be examined using an electronic endoscope, comprising:
    endoscopic image data generating means for processing the image signal and generating endoscopic image data;
    detecting means that detects at least one of a type of electronic endoscope connected to the endoscopic image processing system which is detected based on information inherent to the electronic endoscope, and a type of the image pickup device incorporated in the connected electronic endoscope;
    mask area setting means for setting a mask area that corresponds to at least one of the electronic endoscope type based on the information inherent to the electronic endoscope and the type of image pickup device detected by the detecting means, and outputting a mask signal;
    image processing means that performs predetermined processing on the endoscopic image data, according to the level of the endoscopic image data and generates processed image data; and
    image synthesizing means for synthesizing the processed image data with the mask area in the endoscopic image data, based on the mask signal.

2. An endoscopic image processing system according to claim 1, wherein the mask area setting means designates a domain not based on the type of the electronic endoscope or the type of image pickup device; further comprising:
    selecting means that selects the mask area that corresponds to the type of the electronic endoscope or the type of the image pickup device or the domain not based on the type of electronic endoscope or the type of image pickup device; and
    control means that extends control so that the image processing means will perform the predetermined processing on the domain selected by the selecting means.

3. An endoscopic image processing system that processes an image signal produced by picking up the image of an intracavitary region of an object to be examined using an electronic endoscope, comprising:
    endoscopic image data generating means for processing the image signal and generating endoscopic image data;
    detecting means that detects a type of image pickup device incorporated in an electronic endoscope connected to the endoscopic image processing system;
    mask area setting means for setting a mask area that corresponds to the type of image pickup device detected by the detecting means, and outputting a mask signal;
    image processing means that performs predetermined processing on the endoscopic image data, according to the level of the endoscopic image data and generates processed image data; and
    image synthesizing means for synthesizing the processed image data with the mask area in the endoscopic image data, based on the mask signal.

4. An endoscopic image processing system according to claim 3, wherein the mask area setting means designates a domain not based on the type of the electronic endoscope or the type of the image pickup device, further comprising:
    selecting means that selects the mask area that corresponds to the type of the electronic endoscope or the type of the image pickup device or the domain not based on the type of the electronic endoscope or the type of the image pickup device; and
    control means that extends control so that the image processing means performs the predetermined processing on the domain selected by the selecting means.

5. An endoscopic image processing system according to claim 1, wherein the image processing means serves as hematic information calculating means that calculates hematic information, and generates quasi color image data based on the hematic information.

6. An endoscopic image processing system according to claim 1, further comprising image transmitting means that transmits an image, which is represented by the mask area corresponding to at least one of the type based on the information inherent to the electronic endoscope, and the type of the image pickup device detected by the detecting means, dealt with by the image processing means, as an image represented by the first domain within the image data.

7. An endoscopic image processing system that produces a signal representing an endoscopic image of the interior of an object to be examined, comprising:
    endoscopic image data generating means for processing the image signal and generating endoscopic image data;
    image processing means that performs on the endoscope image data predetermined image processing to deal with hematic information concerning the object to be examined according to the level of the endoscopic image data and generating processed image data;

detecting means that detects at least one of a type of electronic endoscope connected to the endoscopic image processing system which is detected based on information inherent to the electronic endoscope, and a type of image pickup device incorporated in the connected electronic endoscope;

mask area setting means for setting a mask area that represents a predetermined area for displaying the processed image corresponding to at least one of the type based on the information inherent to the electronic endoscope and the type of image pickup device detected by the detecting means, and outputting a mask signal;

image synthesizing means for synthesizing the processed image data with the mask area in the endoscopic image data, based on the mask signal; and second image processing means that performs second image processing on synthesized image data generated by the image synthesizing means by synthesizing the endoscopic image data and the processed image data, the second image processing being different from the predetermined image processing that deals with the hematic information, on the succeeding stage.

8. An endoscopic image processing system according to claim 7, further comprising a control means that when a processed image having undergone at least the predetermined image processing is displayed, disables the image processing to be performed on the processed image, which is to be displayed, by the second image processing means.

9. An endoscopic image processing system according to claim 8, wherein, when an image other than the processed image having undergone the predetermined image processing is dealt with, enabling or disabling of the image processing to be performed by the second image processing means can be selected.

10. An endoscopic image processing system according to claim 8, wherein when the display of the processed image is canceled, the action of the second image processing means is enabled.

11. An endoscopic image processing system that produces a signal representing an endoscopic image of the interior of an object to be examined, comprising:

endoscopic image data generating means for processing the image signal and generating endoscopic image data;

image processing means that performs on the endoscopic image data predetermined image processing to deal with hematic information concerning the object to be examined according to the level of the endoscopic image data, and generating processed image data;

detecting means that detects at least one of a type of electronic endoscope connected to the endoscopic image processing system which is detected based on information inherent to the electronic endoscope, and a type of image pickup device incorporated in the connected electronic endoscope;

mask area setting means for setting a mask area that represents a predetermined area for displaying the processed image corresponding to at least one of the type based on the information inherent to the electronic endoscope and the type of image pickup device detected by the detecting means, and outputting a mask signal;

image synthesizing means for synthesizing the processed image data with the mask area in the endoscopic image data, based on the mask signal; and color enhancing means that performs color enhancement processing on synthesized image data generated by the image synthesizing means by synthesizing the endoscopic image data and the processed image data, the color enhancement processing being different from the predetermined image processing that deals with the hematic information, on the succeeding stage.

12. An endoscopic image processing system according to claim 11, wherein:

the color enhancing means includes a luminance detecting means that detects a luminance level, and an enhancement level designating means that designates an enhancement level; and depending on whether the enhancement level is equal to or larger than a certain value or smaller than the certain value, the limit of a degree of enhancement to be designated by a degree-of-enhancement designating means realized by the luminance detecting means is varied.

13. An endoscopic image processing system according to claim 5, wherein the image processing means performs processing to calculate a value correlating to an amount of hemoglobin from image signals, which are obtained by the electronic endoscope and separated to red, green and blue color signals, calculates a value correlating to an amount of hemoglobin in each image and an average value thereof, and generates a quasi color image based on the value correlating to the amount of hemoglobin.

14. An endoscopic image processing system according to claim 7, wherein the second image processing means performs at least one of gamma correction and structure enhancement on the endoscopic image data surrounding the mask area, with respect to the synthesized image data of the endoscopic image data and the processed image data obtained by the image synthesizing means.

15. An endoscopic image processing system according to claim 5, further comprising means that turns on and off display of the quasi color image data, which outputs only the endoscopic image data to a display means when the display of the quasi color image is turned off.

* * * * *